(12) United States Patent
Orban, III et al.

(10) Patent No.: US 7,727,244 B2
(45) Date of Patent: Jun. 1, 2010

(54) STERILE SURGICAL DRAPE

(75) Inventors: Joseph Orban, III, Norwalk, CT (US); Lisa Heaton, Huntington, CT (US); S. Christopher Anderson, Northamton, MA (US); Thomas G Cooper, Menlo Park, CA (US)

(73) Assignee: Intuitive Surgical Operation, Inc., Sunnyvale, CA (US)

( * ) Notice: Subject to any disclaimer, the term of this patent is extended or adjusted under 35 U.S.C. 154(b) by 1034 days.

(21) Appl. No.: 11/240,113

(22) Filed: Sep. 30, 2005

(65) Prior Publication Data
US 2006/0161137 A1 Jul. 20, 2006

Related U.S. Application Data

(63) Continuation-in-part of application No. 10/922,346, filed on Aug. 19, 2004, now Pat. No. 7,357,774, which is a continuation of application No. 10/004,399, filed on Oct. 30, 2001, now abandoned, which is a continuation of application No. 09/406,360, filed on Sep. 28, 1999, now Pat. No. 6,346,072, which is a continuation of application No. 08/975,617, filed on Nov. 21, 1997, now Pat. No. 6,132,368.

(51) Int. Cl.
*A61B 19/02* (2006.01)
(52) U.S. Cl. .................. 606/130; 600/102; 128/849
(58) Field of Classification Search ................ 600/102, 600/121, 125; 606/1, 130; 128/849, 853, 128/854, 856
See application file for complete search history.

(56) References Cited

U.S. PATENT DOCUMENTS 1,535,312 A * 4/1925 Hosking ...................... 352/242
3,528,720 A * 9/1970 Treace ......................... 359/510
3,698,791 A * 10/1972 Walchle et al. .............. 359/510
4,045,118 A * 8/1977 Geraci ........................ 359/510
4,099,614 A * 7/1978 Heissenberger ............. 206/299
4,183,613 A * 1/1980 Walchle et al. .............. 359/510
4,561,540 A * 12/1985 Hunter et al. ............... 209/305

(Continued)

FOREIGN PATENT DOCUMENTS

JP 7-194610 8/1995

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

(Continued)

*Primary Examiner*—John P Leubecker

(57) ABSTRACT

An improved sterile drape, system, and method for draping portions of a telerobotic surgical system are provided. In one embodiment, a sterile drape includes an exterior surface adjacent to a sterile field for performing a surgical procedure, and an interior surface forming a cavity for receiving the non-sterile portion of a robotic surgical system, such as a manipulator. The drape further includes a fastener coupled to the exterior surface for securing the sterile drape to the non-sterile portion of the robotic surgical system while reducing the volume of the sterile drape. Advantageously, the drape allows for quick and simple installation and increases visualization of the patient by reducing the size of the drape with more form fitting features, while allowing for freedom of movement of the manipulator.

26 Claims, 24 Drawing Sheets

U.S. PATENT DOCUMENTS

| | | | |
|---|---|---|---|
| 4,799,779 A | | 1/1989 | Mesmer |
| 4,905,710 A | * | 3/1990 | Jones ........................ 128/849 |
| 5,080,108 A | * | 1/1992 | Roth ......................... 128/849 |
| 5,122,904 A | * | 6/1992 | Fujiwara et al. ............. 359/510 |
| 5,274,500 A | | 12/1993 | Dunn |
| 5,429,142 A | * | 7/1995 | Szabo et al. ................ 128/849 |
| 5,433,221 A | * | 7/1995 | Adair ........................ 128/849 |
| 5,441,042 A | * | 8/1995 | Putman ...................... 600/102 |
| 5,458,132 A | * | 10/1995 | Yabe et al. .................. 600/121 |
| 5,490,524 A | * | 2/1996 | Williams et al. ............ 128/849 |
| 5,631,832 A | | 5/1997 | Hagenbuch |
| 5,631,973 A | | 5/1997 | Green |
| 5,732,712 A | * | 3/1998 | Adair ........................ 128/845 |
| 5,765,565 A | * | 6/1998 | Adair ........................ 128/849 |
| 5,853,363 A | * | 12/1998 | Vought ...................... 600/121 |
| 5,873,814 A | * | 2/1999 | Adair ........................ 600/109 |
| 5,876,328 A | * | 3/1999 | Fox et al. ................... 600/122 |
| 5,931,832 A | | 8/1999 | Jensen |
| 5,970,980 A | * | 10/1999 | Adair ........................ 128/849 |
| 6,102,850 A | * | 8/2000 | Wang et al. ................ 600/102 |
| 6,123,080 A | * | 9/2000 | Mohan et al. .............. 128/849 |
| 6,132,368 A | | 10/2000 | Cooper |
| 6,167,884 B1 | * | 1/2001 | Navis ........................ 128/849 |
| 6,331,181 B1 | | 12/2001 | Tierney et al. |
| 6,346,072 B1 | | 2/2002 | Cooper |
| 6,451,027 B1 | | 9/2002 | Cooper et al. |
| 6,491,701 B2 | | 12/2002 | Tierney |
| 6,612,310 B2 | * | 9/2003 | Sklar ......................... 128/849 |
| 6,770,081 B1 | | 8/2004 | Cooper |
| 6,805,453 B2 | * | 10/2004 | Spetzler et al. ............. 359/510 |
| 7,074,180 B2 | * | 7/2006 | Bertolero et al. ............ 600/101 |
| 7,122,032 B2 | * | 10/2006 | Shinmura et al. ............. 606/34 |
| 2002/0069882 A1 | * | 6/2002 | Sklar ......................... 128/849 |
| 2003/0006653 A1 | | 4/2003 | Spetzler et al. |
| 2003/0153810 A1 | * | 8/2003 | Bertolero et al. ............ 600/101 |
| 2004/0049205 A1 | * | 3/2004 | Lee et al. .................... 606/130 |
| 2004/0127891 A1 | * | 7/2004 | Humble et al. ................. 606/1 |
| 2007/0043338 A1 | * | 2/2007 | Moll et al. .................... 606/1 |

OTHER PUBLICATIONS

U.S. Appl. No. 08/517053.
U.S. Appl. No. 10/004399.
U.S. Appl. No. 10/922346.
U.S. Appl. No. 11/240,087.
PCT/US06/ 37432 International Search Report, mailed Dec. 15, 2006, 4 pages.
PCT/US06/37432 Written Opinion of the International Search Authority, mailed Dec. 15, 2006, 7 pages.

* cited by examiner

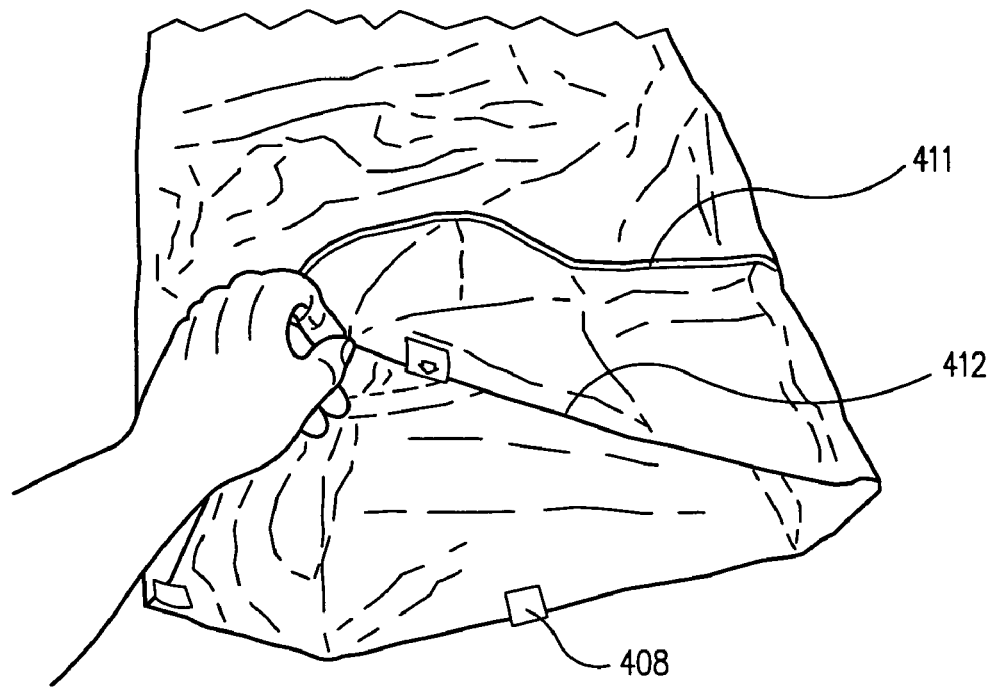
FIG. 11G1
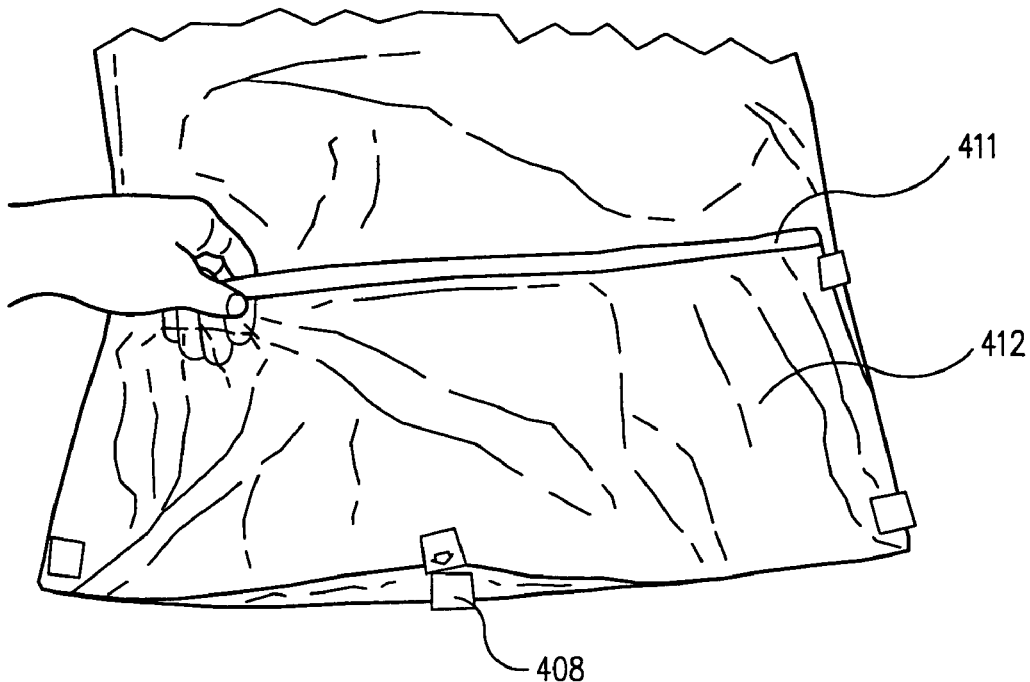
FIG. 11G2

STERILE SURGICAL DRAPE

CROSS-REFERENCE TO RELATED APPLICATIONS

This application is a continuation-in-part of U.S. patent application No. 10/922,346, filed Aug. 19, 2004, now U.S. Pat. No. 7,357,774, which is a continuation of U.S. patent application Ser. No. 10/004,399, filed Oct. 30, 2001, now abandoned, which is a continuation of U.S. patent application Ser. No. 09/406,360, filed Sept. 28, 1999, now U.S. Pat. No. 6,346,072, which is a continuation of U.S. patent application Ser. No. 08/975,617, filed Nov. 21, 1997, now U.S. Pat. No. 6,132,368, the full disclosures of which are hereby incorporated by reference for all purposes.

TECHNICAL FIELD

The present invention relates generally to surgical robot systems and, more particularly, to sterile drapes for covering portions of the surgical robot system.

BACKGROUND

In robotically-assisted or telerobotic surgery, the surgeon typically operates a master controller to remotely control the motion of surgical instruments at the surgical site from a location that may be remote from the patient (e.g., across the operating room, in a different room or a completely different building from the patient). The master controller usually includes one or more hand input devices, such as joysticks, exoskeletal gloves or the like, which are coupled to the surgical instruments with servo motors for articulating the instruments at the surgical site. The servo motors are typically part of an electromechanical device or surgical manipulator ("the slave") that supports and controls the surgical instruments that have been introduced directly into an open surgical site or through trocar sleeves into a body cavity, such as the patient's abdomen. During the operation, the surgical manipulator provides mechanical articulation and control of a variety of surgical instruments, such as tissue graspers, needle drivers, electrosurgical cautery probes, etc., that each perform various functions for the surgeon, e.g., holding or driving a needle, grasping a blood vessel, or dissecting, cauterizing or coagulating tissue.

This new method of performing telerobotic surgery through remote manipulation has, of course, created many new challenges. One such challenge results from the fact that a portion of the electromechanical surgical manipulator will be in direct contact with the surgical instruments, and will also be positioned adjacent the operation site. Accordingly, the surgical manipulator may become contaminated during surgery and is typically disposed of or sterilized between operations. From a cost perspective, it would be preferable to sterilize the device. However, the servo motors, sensors, encoders, and electrical connections that are necessary to robotically control the motors typically cannot be sterilized using conventional methods, e.g., steam, heat and pressure, or chemicals, because the system parts would be damaged or destroyed in the sterilization process.

A sterile drape has been previously used to cover the surgical manipulator but the drape may at times be difficult or time-consuming to install, limit movement of the surgical manipulator, or hinder the surgeon's view of the surgical site. Prior drapes have also at times hindered visibility or touching of the monitor screen.

What is needed, therefore, are telerobotic systems, apparatus, and methods for minimizing the need for sterilization to improve cost efficiency while protecting the system and the surgical patient. In addition, these systems and methods should be designed to be simple to install and to minimize installation time while allowing for maximum freedom of movement and visibility during the surgical procedure. Accordingly, a sterile drape, system, and method for robotic surgery having improved efficiency and effectiveness are highly desirable.

SUMMARY

The present invention provides an improved sterile drape, system, and method for draping of portions of a telerobotic surgical system.

In accordance with an embodiment of the present invention, a sterile drape to cover a non-sterile portion of a robotic surgical system is provided, the sterile drape including an exterior surface adjacent to a sterile field for performing a surgical procedure, and an interior surface forming a cavity for receiving the non-sterile portion of the robotic surgical system. The drape further includes a fastener coupled to the exterior surface for securing the sterile drape to the non-sterile portion of the robotic surgical system while reducing the volume of the sterile drape.

In accordance with another embodiment of the present invention, a robotic surgical system for performing a procedure within a sterile field is provided, the system including a manipulator arm, a monitor, and a sterile drape similar to that described above and including an interior surface forming cavities for receiving the manipulator arm and the monitor, and a plurality of fasteners for securing the sterile drape to the manipulator arm and the monitor.

In accordance with yet another embodiment of the present invention, a method of draping a robotic surgical system is provided, the method including providing a sterile drape similar to that described above and including an open end with an integral cuff, positioning the open end at a portion of the robotic surgical system, holding the integral cuff to unfold the sterile drape over the portion of the robotic surgical system, and securing the sterile drape to the portion of the robotic surgical system using the fastener.

Advantageously, the present invention provides for improved installation of the drape and improved visibility of the surgical site and monitor while allowing for freedom of movement of the surgical manipulator.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIGS. 11A-11L are views of a PSM drape in accordance with an embodiment of the present invention.

Figure 1:
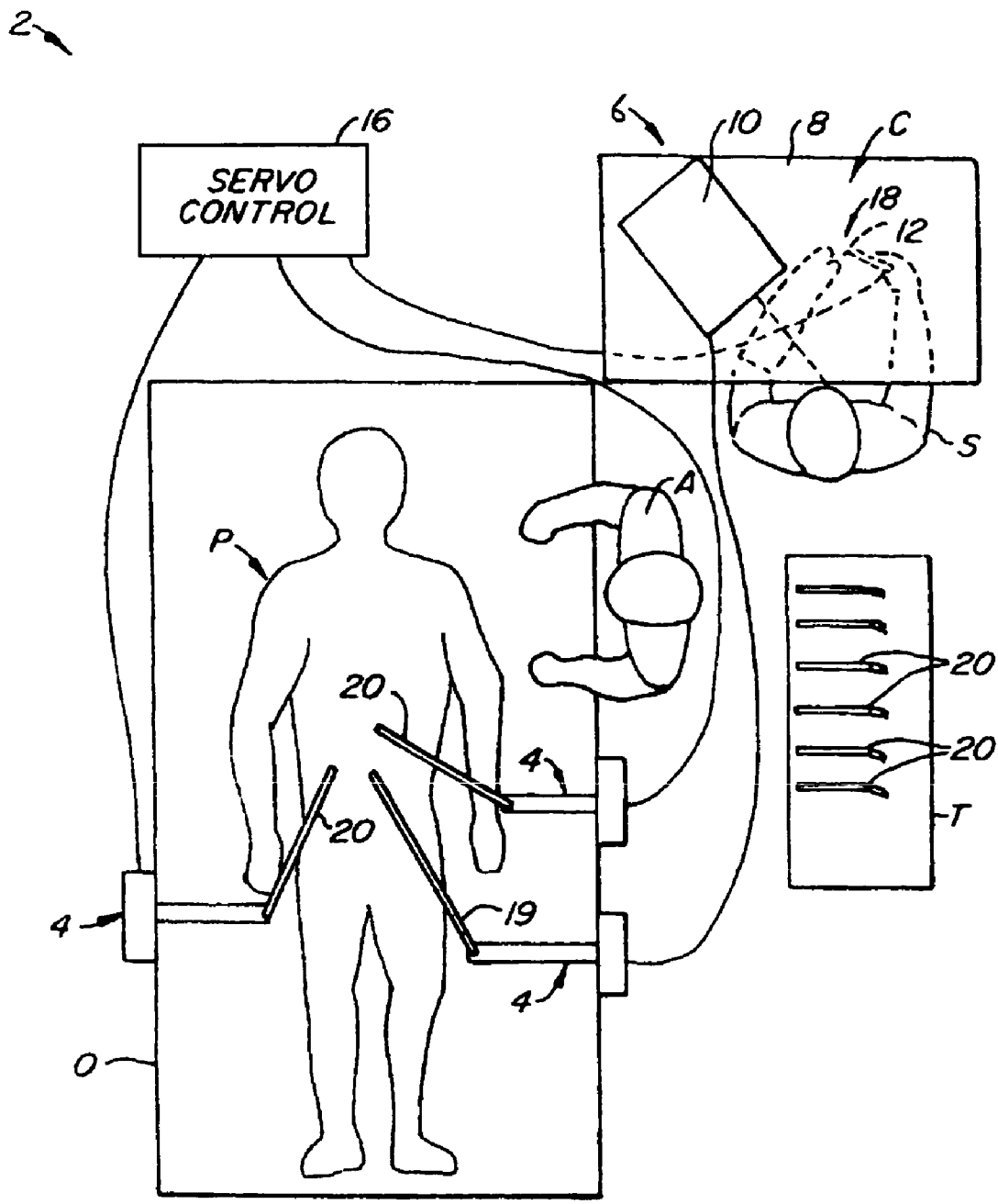
FIG. 1 is a schematic view of an operating room, illustrating a telerobotic surgical system and method in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a multi-component system and method for performing robotically-assisted surgical procedures on a patient, particularly including open surgical procedures, neurosurgical procedures, such as stereotaxy, and endoscopic procedures, such as laparoscopy, arthroscopy, thoracoscopy and the like. The system and method of the present invention is particularly useful as part of a telerobotic surgical system that allows the surgeon to manipulate the surgical instruments through a servomechanism from a remote location from the patient. To that end, the manipulator apparatus or slave of the present invention will usually be driven by a kinematically-equivalent master to form a telepresence system with force reflection. A description of a suitable slave-master system can be found in U.S. patent application Ser. No. 08/517,053, filed Aug. 21, 1995, the complete disclosure of which is incorporated herein by reference for all purposes.

Referring to the drawings in detail, wherein like numerals indicate like elements, a telerobotic surgical system 2 is illustrated according to an embodiment of the present invention. As shown in FIG. 1, telerobotic system 2 generally includes one or more surgical manipulator assemblies 4 mounted to or near an operating table O, and a control assembly 6 for allowing the surgeon S to view the surgical site and to control the manipulator assemblies 4. The system 2 will also include one or more viewing scope assemblies 19 and a plurality of surgical instrument assemblies 20 adapted for being removably coupled to manipulator assemblies 4 (discussed in detail below). Telerobotic system 2 usually includes at least two manipulator assemblies 4 and preferably three manipulator assemblies 4. The exact number of manipulator assemblies 4 will depend on the surgical procedure and the space constraints within the operating room among other factors. As discussed in detail below, one of the assemblies 4 will typically operate a viewing scope assembly 19 (e.g., in endoscopic procedures) for viewing the surgical site, while the other manipulator assemblies 4 operate surgical instruments 20 for performing various procedures on the patient P.

Control assembly 6 may be located at a surgeon's console C which is usually located in the same room as operating table O so that the surgeon may speak to his/her assistant(s) A and directly monitor the operating procedure. However, it should be understood that the surgeon S can be located in a different room or a completely different building from the patient P. Control assembly 6 generally includes a support 8, a monitor 10 for displaying an image of the surgical site to the surgeon S, and one or more controller(s) 12 for controlling manipulator assemblies 4. Controller(s) 12 may include a variety of input devices, such as joysticks, gloves, trigger-guns, hand-operated controllers, voice recognition devices or the like. Preferably, controller(s) 12 will be provided with the same degrees of freedom as the associated surgical instrument assemblies 20 to provide the surgeon with telepresence, or the perception that the controller(s) 12 are integral with the instruments 20 so that the surgeon has a strong sense of directly controlling instruments 20. Position, force, and tactile feedback sensors (not shown) may also be employed on instrument assemblies 20 to transmit position, force, and tactile sensations from the surgical instrument back to the surgeon's hands as he/she operates the telerobotic system. One suitable system and method for providing telepresence to the operator is described in U.S. patent application Ser. No. 08/517,053, filed Aug. 21, 1995, which has previously been incorporated herein by reference.

Monitor 10 will be suitably coupled to the viewing scope assembly 19 such that an image of the surgical site is provided adjacent the surgeon's hands on surgeon console C. Preferably, monitor 10 will display an inverted image on a display 18 that is oriented so that the surgeon feels that he or she is actually looking directly down onto the operating site. To that end, an image of the surgical instruments 20 appears to be located substantially where the operator's hands are located even though the observation points (i.e., the endoscope or viewing camera) may not be from the point of view of the image. In addition, the real-time image is preferably transformed into a perspective image such that the operator can manipulate the end effector and the hand control as if viewing the workspace in substantially true presence. By true presence, it is meant that the presentation of an image is a true perspective image simulating the viewpoint of an operator that is physically manipulating the surgical instruments 20. Thus, a controller (not shown) transforms the coordinates of the surgical instruments 20 to a perceived position so that the perspective image is the image that one would see if the camera or endoscope was located directly behind the surgical instruments 20. A suitable coordinate transformation system for providing this virtual image is described in U.S. patent application Ser. No. 08/239,086, filed May 5, 1994, now U.S. Pat. No. 5,631,973, the complete disclosure of which is incorporated herein by reference for all purposes.

As shown in FIG. 1, a servomechanism 16 is provided for transferring the mechanical motion of controllers 12 to manipulator assemblies 4. Servomechanism 16 may be separate from, or integral with manipulator assemblies 4. Servomechanism 16 will usually provide force and torque feedback from the surgical instruments 20 to the hand-operated controllers 12. In addition, servomechanism 16 will include a safety monitoring controller (not shown) that may freeze or at least inhibit all robot motion in response to recognized conditions (e.g., exertion of excessive force on the patient, "running away" of the manipulator assemblies 4, etc.). The servomechanism preferably has a servo bandwidth with a 3 dB cut off frequency of at least 10 hz so that the system can quickly and accurately respond to the rapid hand motions used by the surgeon. To operate effectively with this system, manipulator assemblies 4 have a relatively low inertia and the drive motors 170 (see FIG. 8) have relatively low ratio gear or pulley couplings. Any suitable conventional or specialized servomechanism may be used in the practice of the present invention, with those incorporating force and torque feedback being particularly preferred for telepresence operation of the system.

Figure 7:
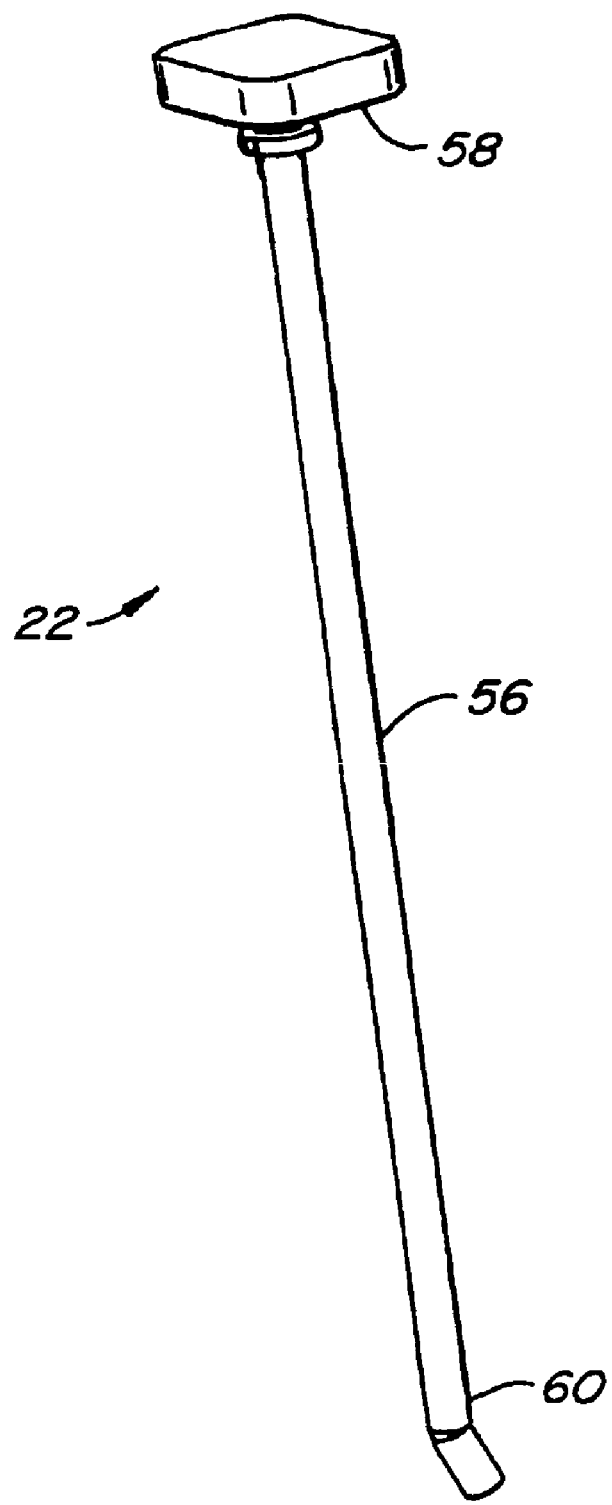
FIG. 7 is a perspective view of the wrist unit in accordance with an embodiment of the present invention.

Referring to FIG. 7, surgical instrument assemblies 20 each include a wrist unit 22 and a surgical tool 24 (FIGS. 3A and 3B) removably attached to wrist unit 22. As discussed in detail below, each wrist unit 22 generally includes an elongate shaft 56 having a proximal cap 58 and a distal wrist 60 pivotally coupled to surgical tool 24. Each wrist unit 22 is substantially the same, and will have different or the same surgical tools 24 attached thereto, depending on the requirements of the surgical procedure. Alternatively, wrist units 22 may have specialized wrists 60 designed for individual surgical tools 24 so that the wrist units 22 may be used with conventional tools 24. As shown in FIG. 1, the instrument assemblies 20 are usually assembled onto a table T or other suitable support adjacent the operating table O. According to a method of the present invention (described below), wrist units 22 and their associated surgical tools 24 can be quickly exchanged during the surgical procedure by coupling and decoupling wrist unit shafts 56 from manipulator assemblies 4.

Figure 2:
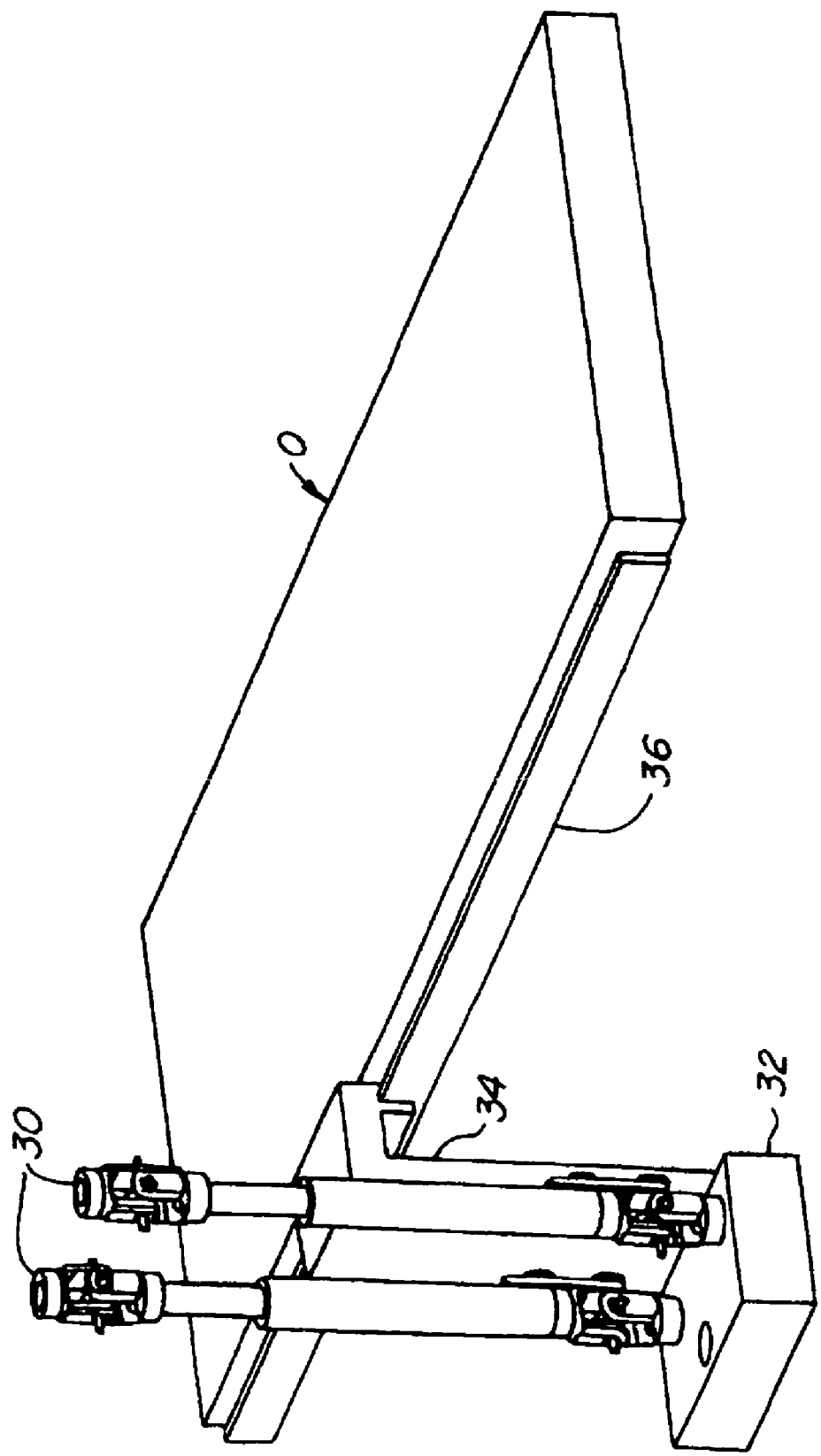
FIG. 2 is an enlarged view of the operating room of FIG. 1 illustrating a pair of mounting joints coupled to an operating table according to the present invention.

Referring to FIG. 2, each manipulator assembly 4 is preferably mounted to operating table O by a mounting joint 30. Mounting joints 30 provide a number of degrees of freedom (preferably at least 5) to assemblies 4, and they include a brake (not shown) so that assemblies 4 can be fixed at a suitable position and orientation relative to the patient. Joints 30 are mounted to a receptacle 32 for mounting joints 30 to operating table O, and for connecting each manipulator assembly 4 to servomechanism 16. In addition, receptacle 32 may connect joints 30 to other systems, such as an RF electrical 2.0 power source, a suction-irrigation system, etc. Receptacle 32 includes a mounting arm 34 that is slidably disposed along an outer rail 36 of operating table O. Manipulator assemblies 4 may also be positioned over the operating table O with other mechanisms. For example, the system may incorporate a support system (coupled to the ceiling or a wall of the operating room) that moves and holds one or more manipulator assemblies 4 over the patient.

Referring now to FIGS. 3-8, manipulator assembly 4 will be described in further detail. Manipulator assembly 4 is a three-component apparatus that includes a non-sterile drive and control component, a sterilizable end effector or surgical tool (i.e., surgical instrument assembly 20), and an intermediate connector component. The intermediate connector includes mechanical elements for coupling the surgical tool 24 with the drive and control component, and for transferring motion from the drive component to the surgical tool 24. As shown in FIG. 3B, the drive and control component generally includes a drive assembly 40 and a multiple degree of freedom robotic arm 42 coupled to a mounting bracket 44, which is adapted for mounting onto mounting joints 30 (FIG. 2). Preferably, drive assembly 40 and robotic arm 42 are pivotally coupled to bracket 44 about an X-axis, which extends through a remote center of spherical rotation 45 (see FIG. 8, discussed in further detail below). Manipulator assembly 4 further includes a forearm assembly 46 fixed to a distal end 48 of arm 42, and a wrist unit adaptor 52 coupled to forearm assembly 46 for mounting wrist unit 22 and surgical tool 24 to manipulator assembly 4.

For endoscopic procedures, manipulator assembly 4 additionally includes a cannula adaptor 64 attached to a lower portion of forearm 46 for mounting a cannula 66 to manipulator assembly 4. Alternatively, cannula 66 may be an integral cannula (not shown) that is built into forearm assembly 46 (i.e., non-removable). Cannula 66 may include a force sensing element (not shown), such as a strain gauge or force-sensing resistor, mounted to an annular bearing within cannula 66. The force sensing bearing supports surgical tool 24 during surgery, allowing the tool to rotate and move axially through the central bore of the bearing. In addition, the bearing transmits lateral forces exerted by the surgical tool 24 to the force sensing element, which is connected to servomechanism 16 for transmitting these forces to controller(s) 12. In this manner, forces acting on surgical tools 24 can be detected without disturbances from forces acting on cannula 66, such as the tissue surrounding the surgical incision, or by gravity and inertial forces acting on manipulator assembly 4. This facilitates the use of manipulator assembly 4 in a robotic system because the surgeon will directly sense the forces acting against the surgical tool 24.

Figure 3A:
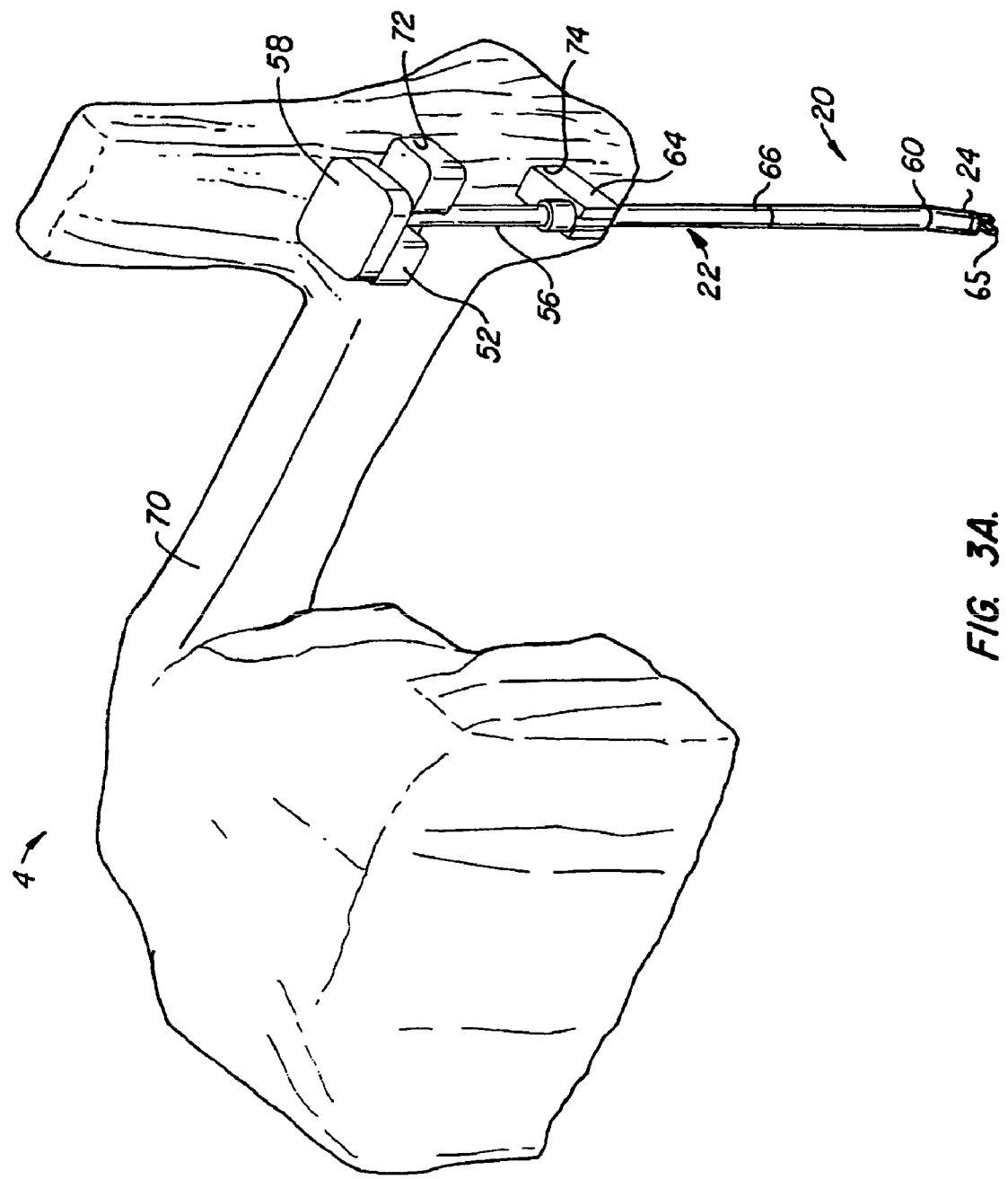
FIG. 3A is a perspective view of a robotic surgical manipulator that is partially covered by a sterile drape in accordance with an embodiment of the present invention.

As shown in FIG. 3A, manipulator assembly 4 further includes a sterile drape 70 sized to cover substantially the entire manipulator assembly 4. Drape 70 has a pair of holes 72, 74 sized and arranged so that wrist unit adaptor 52 and cannula adaptor 64 may extend through holes 72, 74 to mount wrist unit 22 and cannula 66 to manipulator assembly 4. Sterile drape 70 comprises a material configured to effectively shield manipulator assembly 4 from the surgical site so that most of the components of assembly 4 (i.e., arm 42, drive assembly 40 and forearm assembly 46) do not have to be sterilized prior to, or following the surgical procedure.

As shown in FIG. 3A, wrist unit adaptor 52 and cannula adaptor 64 extend through holes 72, 74 of drape 70 so that forearm assembly 46 and the remainder of manipulator assembly 4 remain shielded from the patient during the procedure. In one embodiment, wrist unit adaptor 52 and cannula adaptor 64 are manufactured as reusable components that will be sterilized because these components extend into the sterile field of the surgical site. Wrist unit and cannula adapters 52, 64 may be sterilized by normal methods, i.e., steam, heat and pressure, chemicals and the like. Referring again to FIG. 3B, wrist unit adaptor 52 includes an opening 80 for receiving shaft 56 of wrist unit 22. As discussed in detail below, shaft 56 can be laterally urged through opening 80 and snap-fit into adaptor 52 such that the non-exposed portion of wrist unit adaptor 52 remains sterile (i.e., remains on the sterile side of drape 70 opposite the sterile field). Wrist unit adaptor 52 may also include a latch (not shown) for securing wrist unit 22 therein. Similarly, cannula adaptor 64 includes an opening 82 for snap fitting cannula 66 thereto such that the non-exposed portion of adaptor 64 remains sterile during the surgical procedure.

Figure 4:
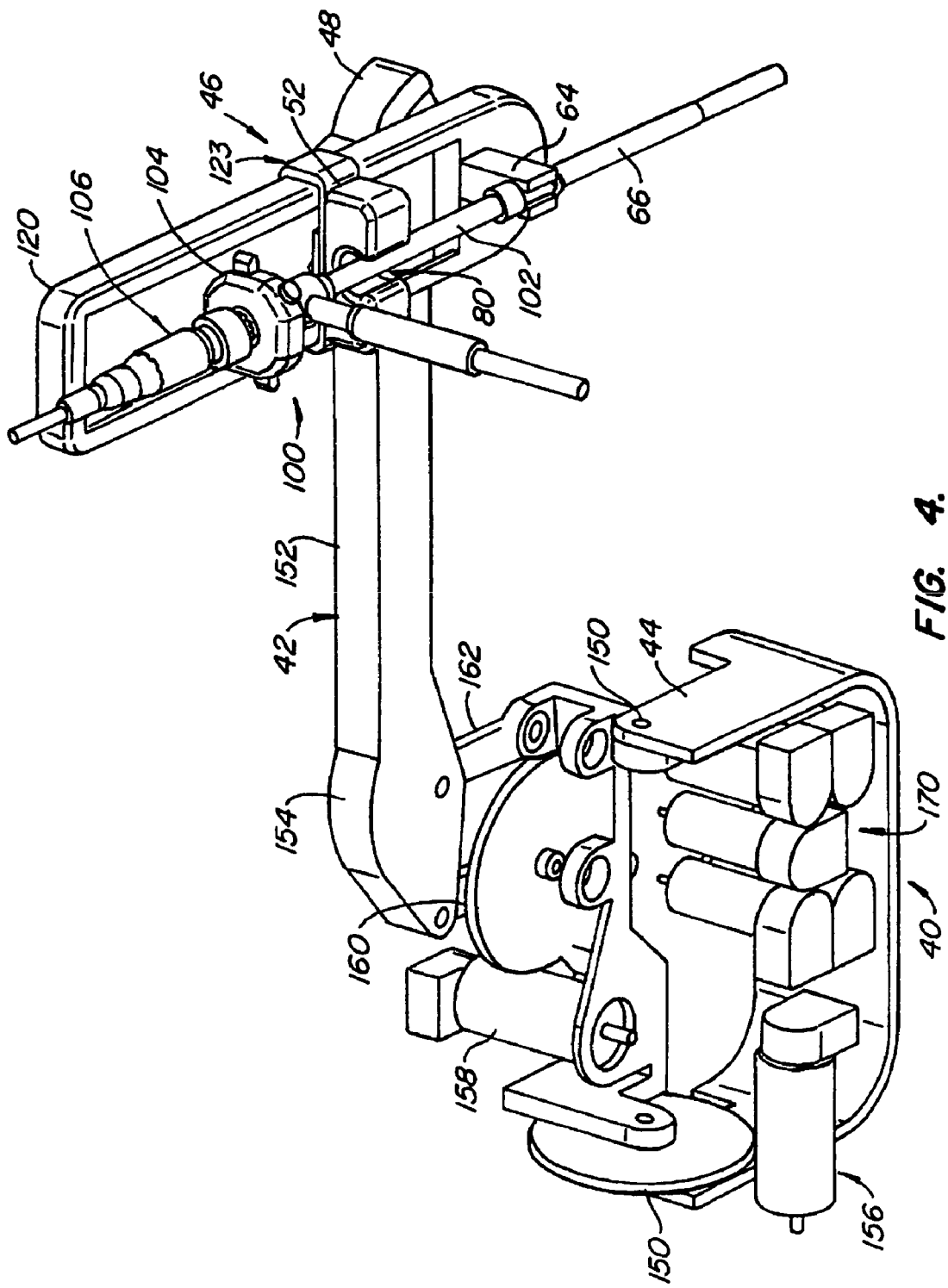
FIG. 4 illustrates the robotic surgical manipulator of FIGS. 3A-3B incorporating a camera and endoscope for viewing the surgical site.

As shown in FIG. 4, wrist unit adaptor 52 may also be configured to receive a viewing scope 100 for viewing the surgical site. For endoscopic procedures, viewing scope 100 can be a conventional endoscope, which typically includes a rigid, elongated tube 102 containing a lens system (not shown) and a camera mount 104 at the proximal end of the tube 102. A small video camera 106 is preferably attached to the camera mount 104 and connected to video monitor 10 to provide a video image of the procedure. Preferably, the scope 100 has a distal end (not shown) configured to allow lateral or angled viewing relative to tube 102. The viewing scope may also have a guidable tip that can be deflected or rotated by manipulating an actuator on a proximal end of tube 102. This type of scope is commercially available from Baxter Healthcare Corp. of Deerfield, Ill., or Origin Medsystems, Inc. of Menlo Park, Calif.

As shown in FIG. 4, viewing scope 100 further includes a scope adaptor 110 for coupling viewing scope 100 to wrist unit adaptor 52. Scope adaptor 110 is sterilizable, ETO and autoclavable, and it includes a plurality of motion feed-throughs (not shown) for transferring motion from drive assembly 40 to scope 100. In the preferred configuration, the motion includes pitch and yaw motion, rotation about the Z-axis, and movement along the Z-axis.

Figure 5:
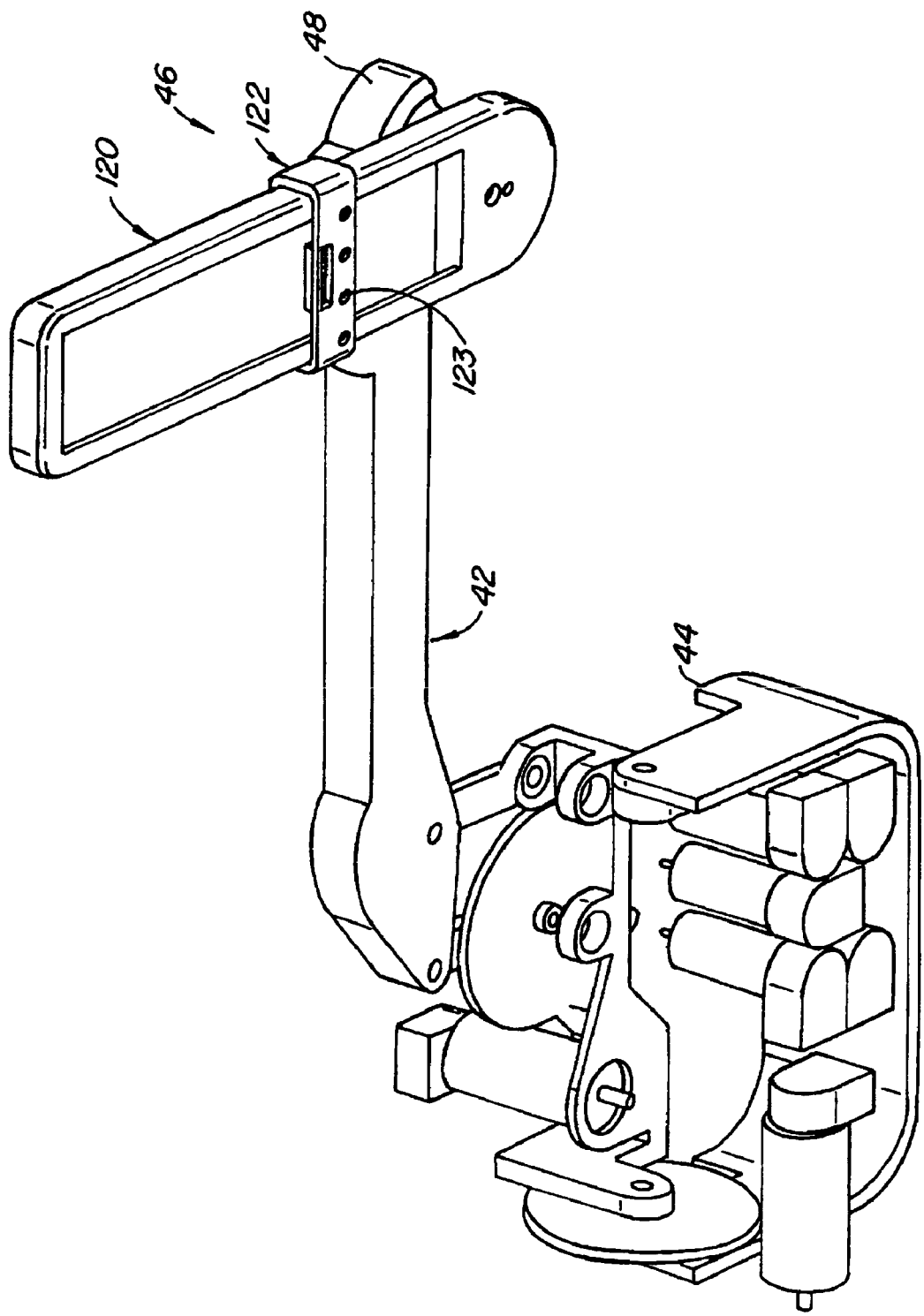
FIG. 5 is a partial view of the robotic manipulator of FIGS. 3A-3B, illustrating mechanical and electrical couplings between the arm and the wrist unit.
Figure 6:
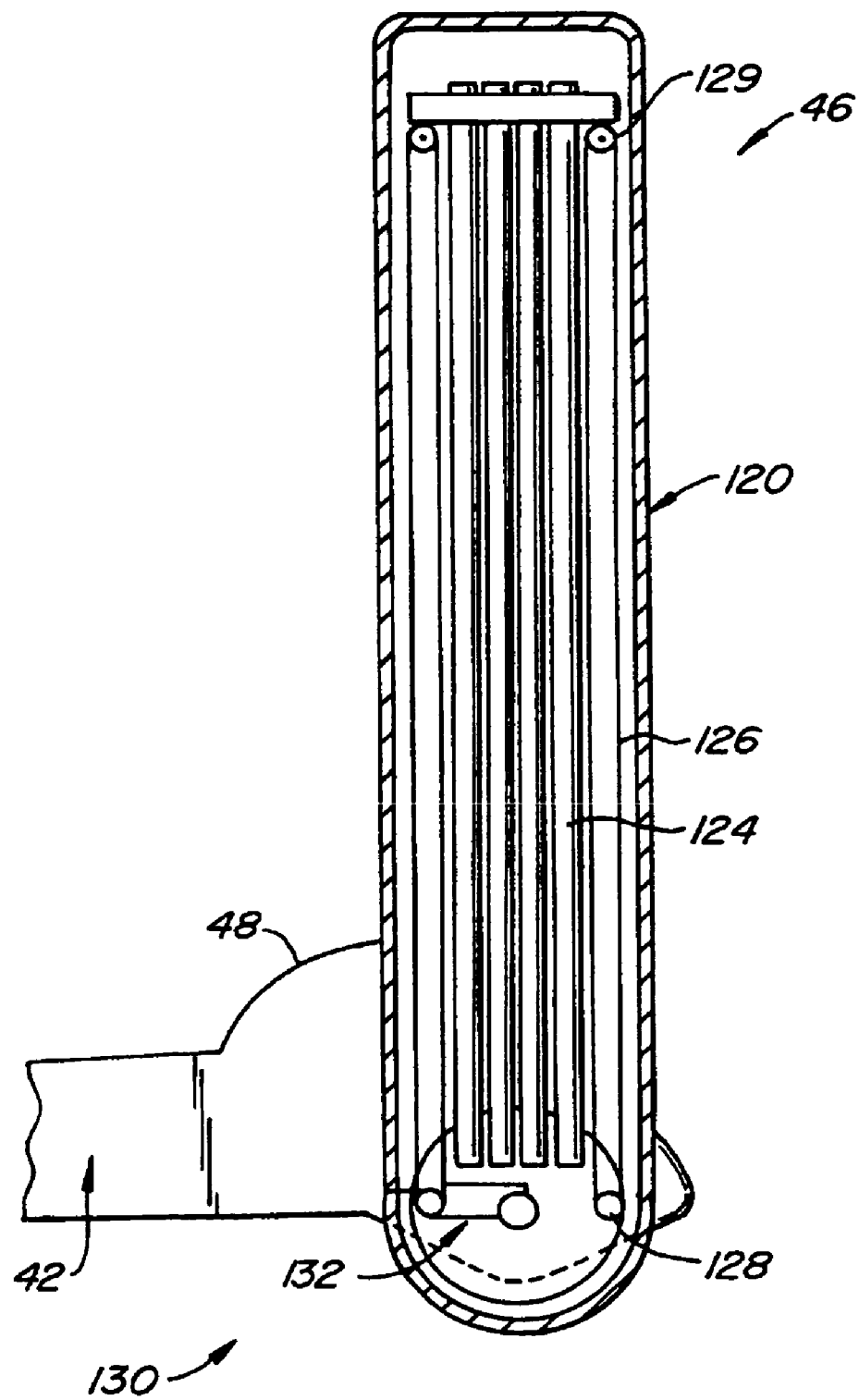
FIG. 6 is a partially cut-away sectional view of a forearm and a carriage of the manipulator of FIGS. 3A and 3B.

Referring now to FIGS. 5 and 6, forearm assembly 46 will be described in further detail. As shown in FIG. 5, forearm assembly 46 includes a housing 120 fixed to arm 42 and a movable carriage 122 slidably coupled to housing 120. Carriage 122 slidably mounts wrist unit adaptor 52 to housing 120 for moving wrist unit adaptor 52 and wrist unit 20 in the Z-direction. In addition, carriage 122 defines a number of openings 123 for transferring motion and electrical signals from forearm assembly 46 to wrist unit adaptor 52. As shown in FIG. 6, a plurality of rotatable shafts 124 are mounted within housing 120 for transferring motion from arm 42 through openings 123 to wrist unit adaptor 52 and wrist unit 22. Rotating shafts 124 preferably provide at least four degrees of freedom to wrist unit 22, including yaw and pitch motion of surgical tool 24 about wrist 60 of wrist unit 22, rotation of wrist unit 22 about the Z-axis and actuation of tool 24. The system may also be configured to provide more or less degrees of freedom, if desired. Actuation of tool 24 may include a variety of motions, such as opening and closing jaws, graspers or scissors, applying clips or staples and the like. Motion of wrist unit 22 and tool 24 in the Z direction is provided by a pair of carriage cable drives 126 extending between rotatable pulleys 128, 129 on either end of forearm housing 120. Cable drives 126 function to move carriage 122 and wrist unit 22 in the Z direction relative to forearm housing 120.

As shown in FIG. 6, distal end 48 of arm 42 includes a coupling assembly 130 having a plurality of motion feed-throughs 132 for transferring motion from arm 42 to forearm assembly 46. In addition, coupling assembly 130 includes a number of electrical connectors (not shown) for transferring electrical signals from arm 42 to wrist unit 22. Similarly, wrist unit adaptor 52 includes a plurality of motion feed-throughs (not shown) and electrical connections (not shown) for transferring motion, and for sending and receiving electrical signals to and from wrist unit 22 (e.g., for sending and receiving force and torque feedback signals from the surgical site to controllers 12). The components on either side of coupling assembly 130 and wrist unit adaptor 52 have a finite range of motion. Usually, this range of motion will be at least 1 revolution and preferably greater than 1 revolution. These ranges of motion are aligned with each other when the forearm assembly 46 is mechanically coupled to the coupling assembly 130 and when wrist unit adaptor 52 is mechanically coupled to the forearm 46.

Referring to FIG. 7, wrist unit 22 will now be described in further detail. As shown, wrist unit 22 includes a hollow shaft 56 having a cap 58 attached to its proximal end and a wrist 60 attached to its distal end. Wrist 60 includes a coupling (not shown) for removably coupling a variety of surgical tools 24 to shaft 56. Shaft 56 is rotatably coupled to cap 58 for providing rotation of shaft 56 and tool 24 about the longitudinal axis of shaft 56 (i.e., the Z axis). Cap 58 houses a mechanism (not shown) for transferring motion from wrist unit adaptor 52 to drive cables (not shown) within shaft 56. The drive cables are suitably coupled to drive pulleys within shaft 56 to pivot tool 24 about wrist 60, and to actuate end effectors 140 on tool 24. Wrist 60 may also be operated by other mechanisms, such as differential gears, push-rods, or the like.

Tool 24 is removably coupled to wrist 60 of wrist unit 22. Tool 24 will preferably include an end effector 65 (FIGS. 3A and 3B) having a tactile sensor array (not shown) for providing tactile feedback to the surgeon. Tool 24 may include a variety of articulated tools, such as jaws, scissors, graspers, needle holders, micro dissectors, staple appliers, tackers, suction irrigation tools, clip appliers, that have end effectors driven by wire links, eccentric cams, push-rods or other mechanisms. In addition, tool 24 may comprise a non-articulated instrument, such as cutting blades, probes, irrigators, catheters or suction orifices. Alternatively, tool 24 may comprise an electrosurgical probe for ablating, resecting, cutting or coagulating tissue. In the latter embodiment, wrist unit 22 will include a conductive element, such as a proximal banana plug coupled to a lead wire or rod extending through shaft 56 to tool 24.

Figure 8:
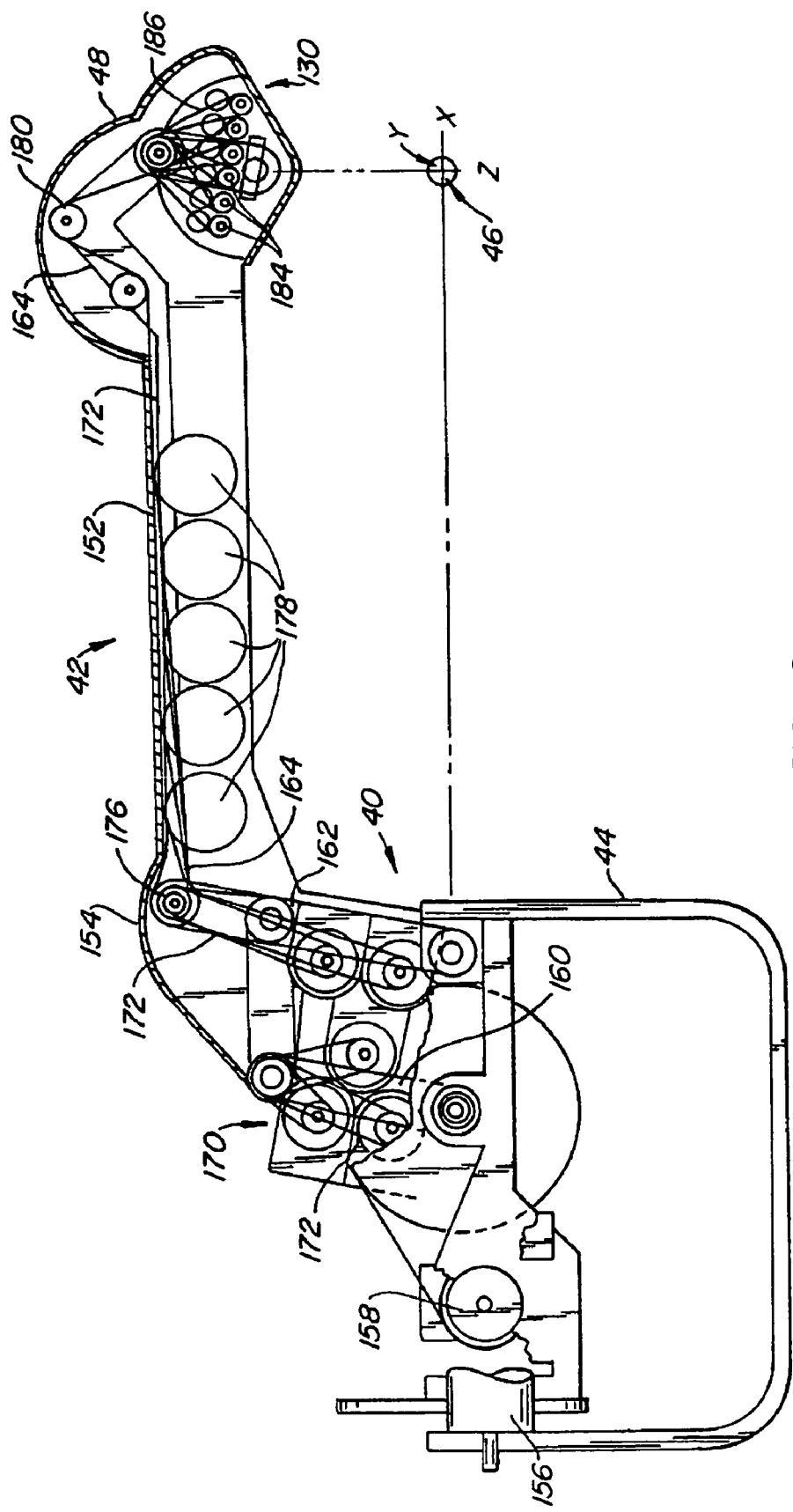
FIG. 8 is a side cross-sectional view of a portion of the robotic manipulator, illustrating the arm and the drive assembly.

Referring to FIGS. 4 and 8, a specific configuration of the drive and control component of the present invention (i.e., the robotic arm 42 and drive assembly 40) will be described in further detail. As discussed above, arm 42 and drive assembly 40 are rotatably coupled about a pair of pins 150 extending from mounting bracket 44. Arm 42 preferably comprises an elongate, substantially rigid body 152 with a distal end 48 coupled to forearm assembly 48 and a proximal end 154 pivotally coupled to drive assembly 40 and bracket 44 for rotation about pitch and yaw or the X and Y axes (note that the Y axis is perpendicular to the page and extends through point 45, see FIG. 8). Arm 40 may have other configurations, such as an elbow arm (similar to the human arm), prismatic arm (straight extendable) or the like. A stationary yaw motor 156 is mounted to mounting bracket 44 for rotating arm 42 and drive assembly 40 about the X-axis. Drive assembly 40 also includes a pitch motor 158 coupled to arm 42 for rotating arm about the Y axis. A pair of substantially rigid linkage elements 160, 124 extend from bracket 44 to robotic arm 42 to pivotally couple arm 42 to bracket 44 about Y-axis. One of the linkage elements 160 is pivotally coupled to arm 42, and the other linkage element 124 is pivotally coupled to a third linkage element 164 extending parallel to arm 42. Preferably, robotic arm 42 is a channel shaped rigid element that at least partially houses the third linkage element 164. The linkage elements 160, 124 and 164 and arm 42 form a parallelogram linkage in which the members are connected together in a parallelogram for relative movement only in the plane formed by the members.

The Z-axis of wrist unit 22 held at the distal end 48 of arm 42 intersects the x axis of the parallelogram linkage described above. Wrist unit 22 has a remote center of spherical rotation about the position indicated by the numeral 45 in FIG. 8. Thus, the distal end of wrist unit 22 can be rotated about its own axis or the X and Y axes while the remote center of rotation 45 remains at the same location. A more complete description of a remote center positioning device can be found in U.S. patent application Ser. No. 08/504,301, filed Jul. 20, 1995, now U.S. Pat. No. 5,931,832, the complete disclosure of which is incorporated herein by reference for all purposes. It should be noted that arm 42 and drive assembly 40 may be used with a broad range of positioning devices other than that described above and shown in FIG. 8, such as a stereotaxic positioner, a fixed gimbal, or the like.

Referring again to FIG. 8, drive assembly 40 further includes a plurality of drive motors 170 coupled to arm 42 for rotation therewith. Pitch and yaw motors 156, 158 control the motion of arm 42 (and drive motors 170) about the X and Y axes and drive motors 170 control the motion of wrist unit 22 and surgical tool 24. Preferably, at least five drive motors 170 are coupled to arm 42 for providing at least five degrees of freedom to wrist unit 22. Drive motors 170 will preferably include encoders (not shown) for responding to servomechanism 16 and force sensors (not shown) for transmitting force and torque feedback to the surgeon S. As discussed above, the five degrees of freedom preferably include movement of carriage 122 and wrist unit 22 in the Z-direction, rotation of wrist unit 22 about the Z-axis, pitch and yaw rotation of surgical tool 24 around wrist 60 and actuation of tool 24.

As shown, cables 172 extend from each motor 170 around a motor drive pulley 174, an idler pulley 176 within arm 42 and along a relatively large pot capstan 178 to minimize the effect of friction torque on cables 172. The cables 172 each extend around another idler pulley 180 at distal end 48 of arm 42, around a coupling drive pulley 182 and back to the motor 170. The cables 172 will preferably be tensioned at the motor drive pulley 174 and anchored there as well as at the coupling drive pulley 182. As shown in FIG. 8, coupling drive pulley 182 is connected to a plurality of smaller pulleys 184 within coupling assembly 130 via a plurality of cables 186 for transferring motion from the motors 170 to wrist unit adaptor 52.

A method for performing a surgical procedure on a patient according to the present invention will now be described with reference to FIGS. 1-8. As shown in FIG. 2, mounting joints 30 are attached to receptacle 32, which is attached to the operating table O by sliding mounting arm 34 along rail 36. Each manipulator assembly 4 is then attached to its respective mounting joint 30 and articulated into the proper position and orientation relative to the patient P. Receptacles 32 are then coupled to servomechanism 16 and other systems that may be required during the surgical procedure, such as an RF power supply, a suction/irrigation system, etc. Sterile drapes 70 are placed over the manipulator assemblies 4 before, during, or after the patient has been anesthetized (FIG. 3A). To prepare for the surgical procedure, manipulator assemblies 4 may or may not be chemically cleaned prior to covering them with drapes 70. Wrist unit adapters 52, cannula adapters 64, and scope adapters 110 are snapped onto forearm assemblies 46 of manipulator assemblies 4 (see FIGS. 3B and 5). The number and relative positions of scope adapters 110 and wrist unit adapters 52 will, of course, depend on the individual surgical procedure (e.g., cannula adapters 64 may not be required for open surgical procedures).

During the surgical procedure, surgical instrument assemblies 20 are coupled to their respective manipulator assemblies 4 by laterally urging each respective wrist unit shaft 56 through opening 80 of wrist unit adaptor 52. Each wrist unit 22 will have suitable identification means (not shown) to quickly and easily indicate what type of tool 24 is connected to the wrist unit 22. When the surgeon wishes to change surgical tools 24, he or she manipulates controller(s) 12 so that carriage 122 moves to a top or proximal position of travel along forearm assembly 46 (see FIG. 3B). In this position, surgical tool 24 is within cannula 66 or during open procedures, removed from the surgical site. The assistant(s) A then pulls upward on wrist cap 58 to release the latch (not shown), thereby allowing wrist unit 22 to slide further upwards and out of cannula 66. The assistant(s) A may then pull wrist unit 22 laterally to decouple it from wrist unit adaptor 52. When wrist unit 22 is no longer coupled to adaptor 52, the control mechanism understands that the system is in "tool change mode", and drives carriage 122 to the proximal position if it has not already been moved there by the surgeon.

Figure 3B:
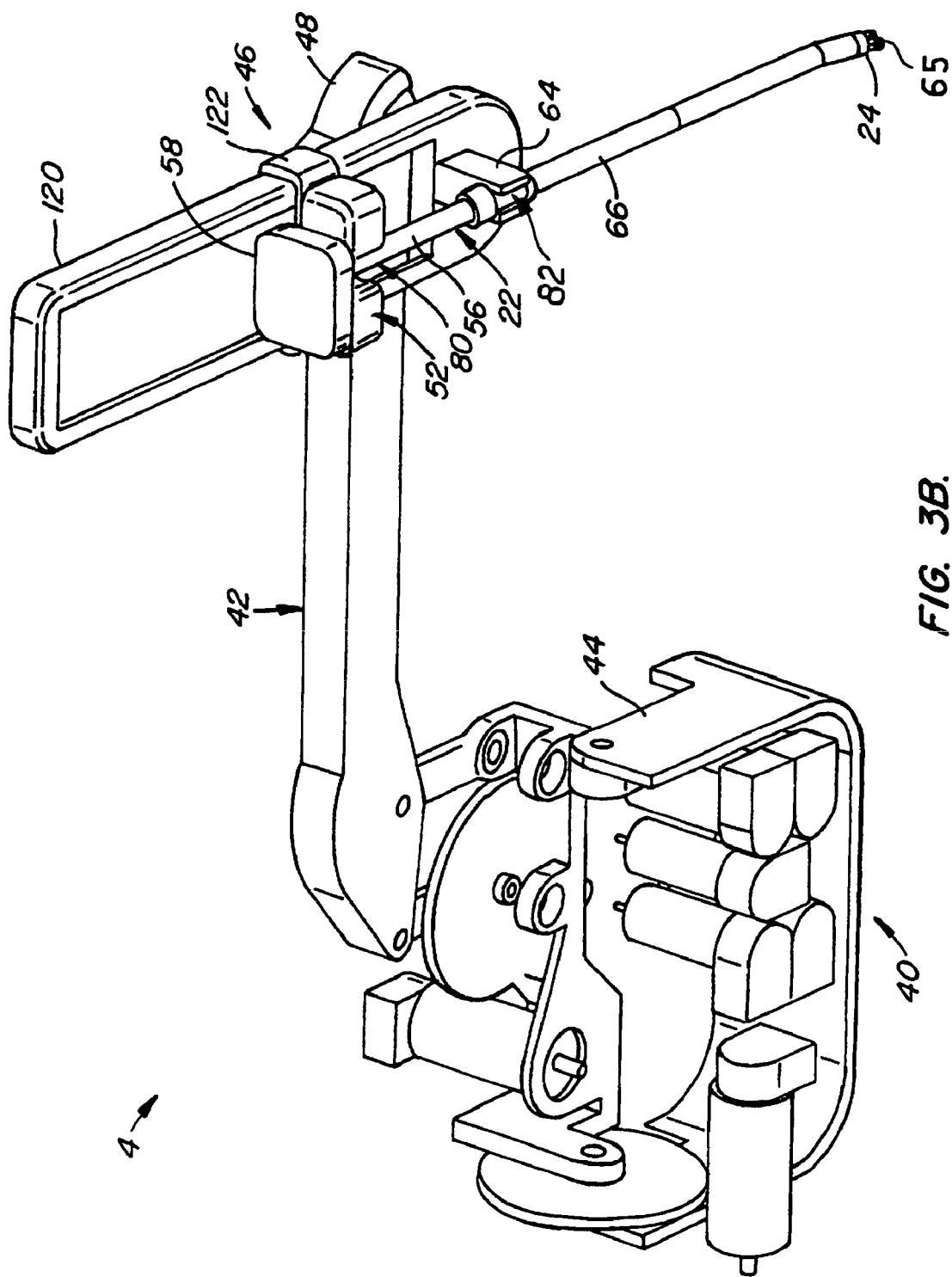
FIG. 3B is a perspective view of the robotic surgical manipulator of FIG. 3A without the sterile drape to illustrate a multiple degree of freedom arm coupling a driving assembly with a wrist unit and a surgical tool.

To couple another surgical instrument assembly 20 to manipulator assembly 4, the assistant(s) A grabs another assembly 20 from table T, laterally urges wrist unit shaft 56 into opening 80 of wrist unit adaptor 52, and then moves wrist unit 22 downward so that surgical tool 24 resides within cannula 66 (see FIGS. 1 and 3B). This downward movement of wrist unit 22 automatically mates the electrical couplings and motion feed-throughs (not shown) within wrist cap 58 and wrist unit adaptor 52. The system may include a control mechanism configured to lock carriage 122 travel at the top or proximal position, e.g., by actuating a brake (not shown), until the couplings are mated and wrist unit 22 is no longer being moved downward. At this point, the surgeon S may continue the surgical procedure.

The system and method of the present invention preferably includes a mechanism for counting the number of times wrist unit 22 is decoupled and coupled from wrist unit adaptor 52. In this manner, the manufacturer may limit the number of times wrist unit 22 can be used. In a specific configuration, an integrated circuit chip (not shown) is housed within wrist cap 58. The circuit chip counts the number of times wrist unit 22 is coupled to wrist unit adaptor 52, e.g., 20 times, and a warning shows up on the surgeon's console C. The control system then downgrades the performance of the system by reducing the load it can deliver or increasing apparent backlash.

Figure 9A:
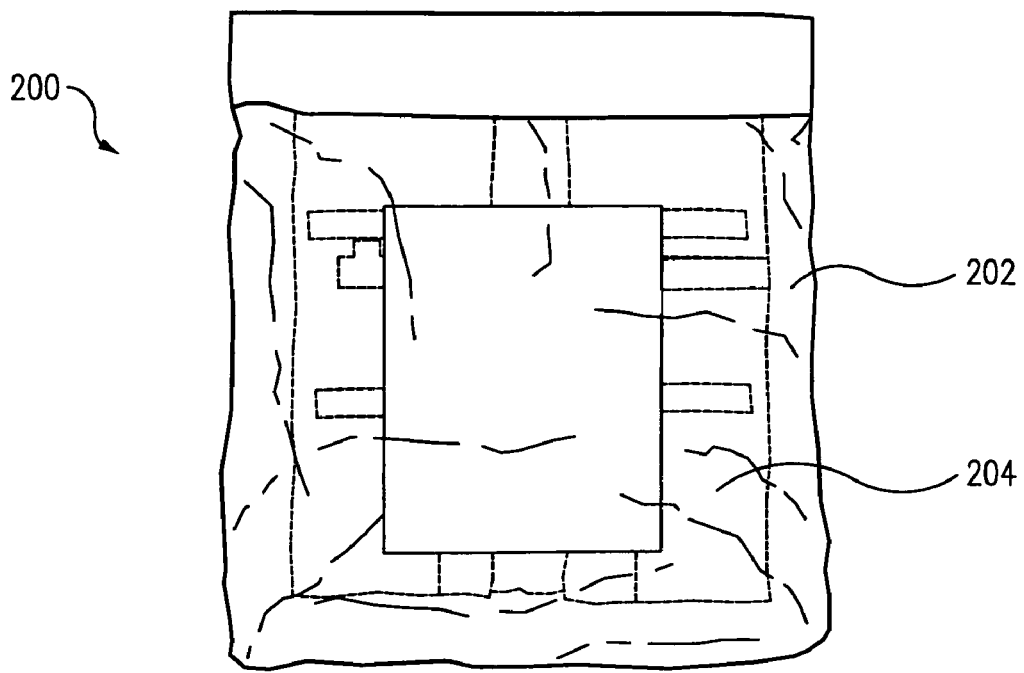
FIGS. 9A-9E are views of a monitor drape in accordance with an embodiment of the present invention.

Referring now to FIGS. 9A-9E, a monitor drape package 200 including a monitor drape 204 that is part of sterile drape 70 (described above with reference to FIG. 3A) is shown. Monitor drape 204 may be a connected or disconnected section of sterile drape 70. FIG. 9A shows monitor drape package 200 including a monitor drape pouch 202 with monitor drape 204 folded inside. Monitor drape 204 is a disposable sterile drape assembly which is placed over a monitor and monitor mount to maintain a sterile barrier between the monitor/monitor mount and the sterile field of the surgical procedure. Advantageously, various features of the monitor drape aid the draping and installation process.

Figure 9B:
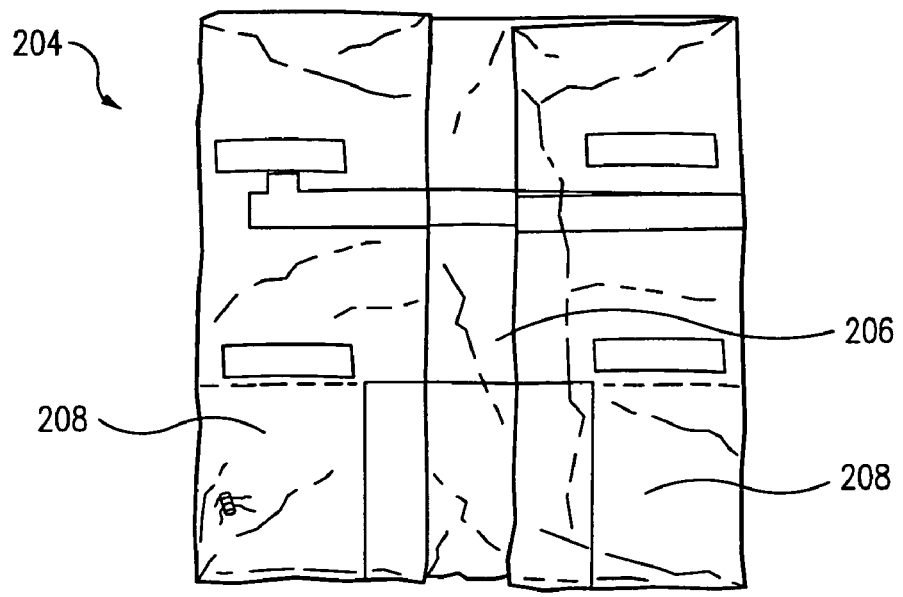

FIG. 9B shows monitor drape 204 removed from pouch 202 with drape 204 including a touch screen window 206 to be placed adjacent to the screen of a monitor (e.g., monitor 10 of FIG. 1). Touch screen window 206 is between two flaps 208 of monitor drape 204 and is not folded to reduce creases and increase adhesion to the monitor screen. In one example, touch screen window 206 is a clear, static-cling window to be positioned in front of the monitor screen. The clear window allows the user to see and use a touch screen monitor while maintaining a sterile barrier. Window 206 has a static charge which maintains a static cling function allowing window 206 to sit flat against the monitor screen to reduce reflections and glare and to keep the window secure for touch screen usage.

Figure 9C:
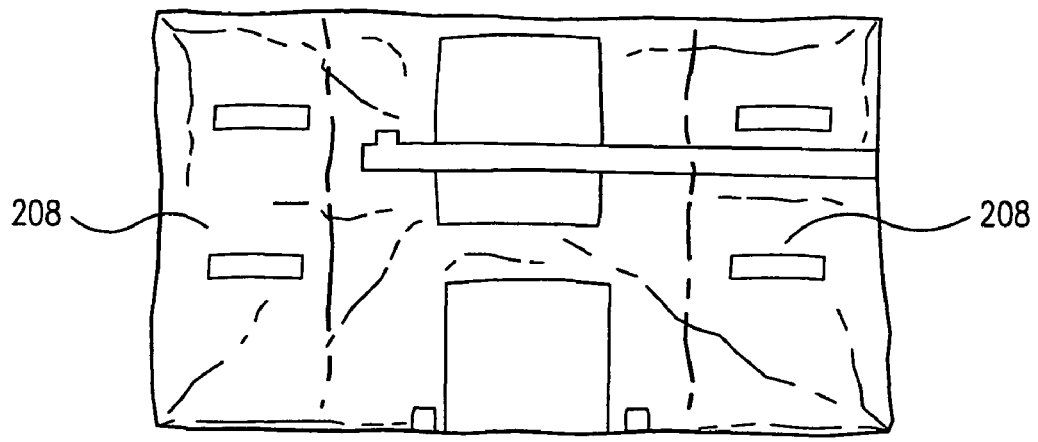

FIG. 9C shows monitor drape 204 with flaps 208 unfolded. As previously noted, monitor drape 204 is folded in a way to assure that the screen window section is not folded, thereby reducing creases in the material and allowing flatter positioning on the monitor screen.

Figure 9D:
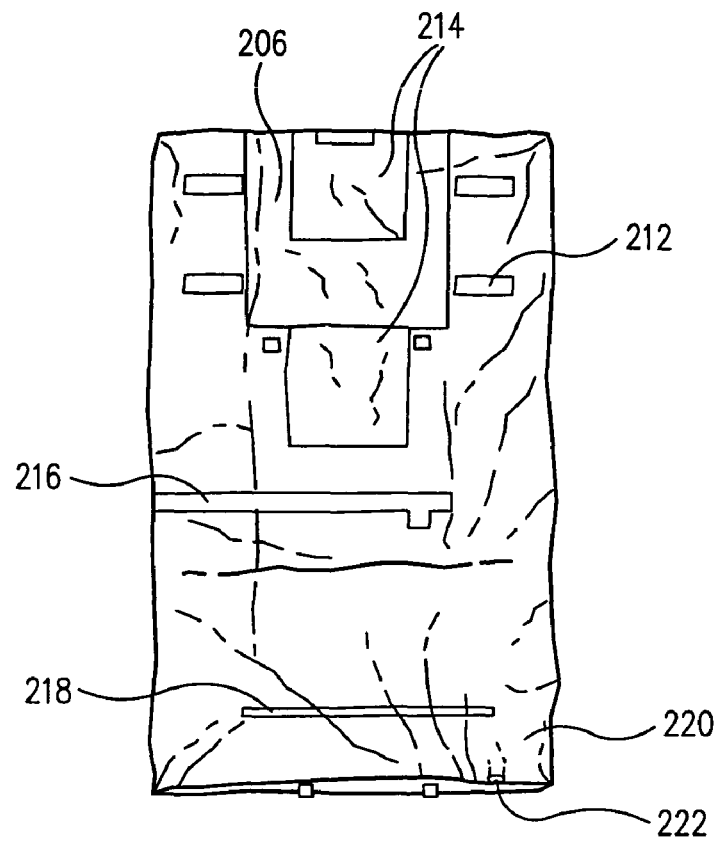

FIG. 9D shows four loop fasteners 212, two vents 214, a strap 216, a permanent cuff 220, a blue tape 218 on the edge of cuff 220, and a purse string 222 built into cuff 220. Loop fasteners 212 are included on either side of screen window 206 on the inside of the drape. Loop fasteners 212 include strips of Velcro which mate with hook fasteners (not shown) located on the back of the monitor mount. These hook and loop fasteners allow the user to quickly pull the drape taught and fixed in position in front of the monitor screen. Vents 214 allow heat generated by the monitor to vent from monitor drape 204. The vents are above and below the monitor area to allow for convection heat venting. Vents 214 also allow for the transmission of sound from the sterile field to a microphone installed proximate the monitor. Straps 216 help control drape 204 and reduce the visual size of the drape (i.e., reduce the volume of or space taken up by the unfolded drape). Blue tape 218 acts as a physical marker on the drape to designate the sterile and non-sterile ends. By having blue tape 218 act as a marker, a non-sterile person can know to pull on the non-sterile side if assisting the sterile scrub nurse. Purse string 222 allows the user to pull monitor drape 204 tight around the monitor mount at the end of the drape.

Figure 9E:
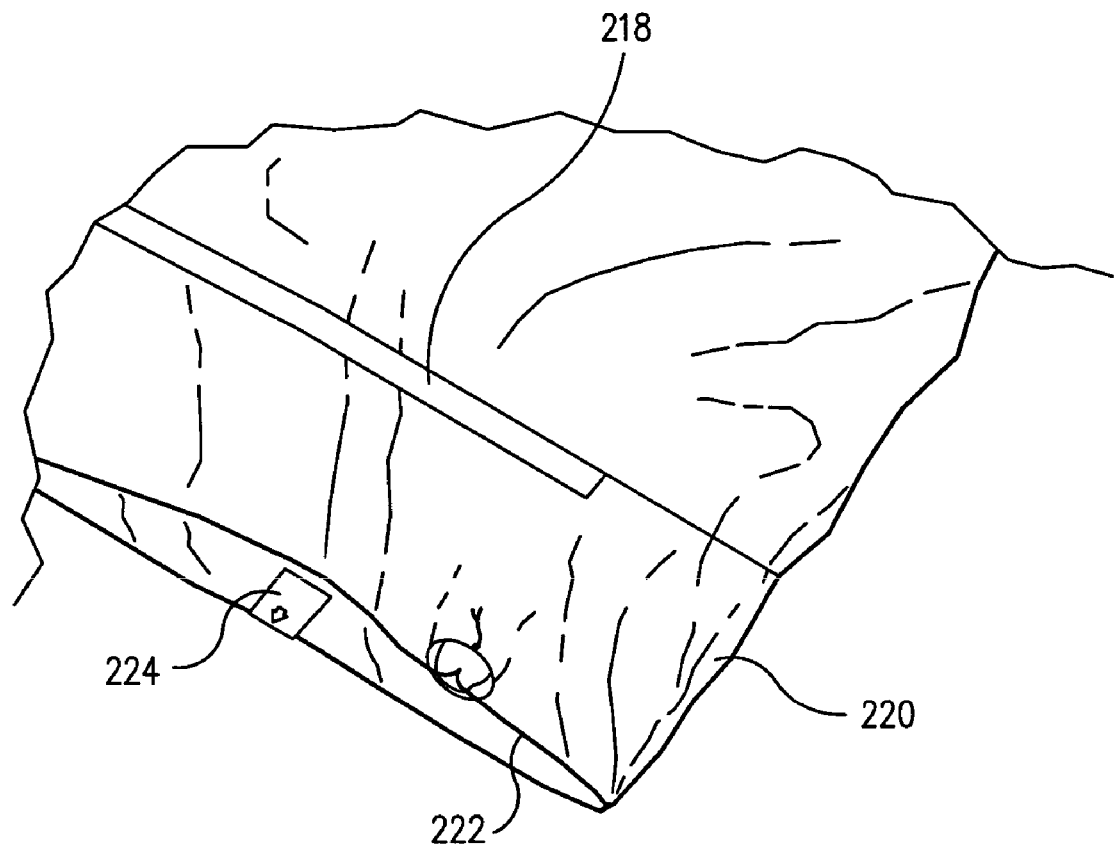

FIG. 9E shows an enlarged view of the drape area proximate cuff 220, including a tear strip 224. Cuff 220 is integral to the end of the drape. A sterile scrub nurse may place his or her hands into these cuffs when pulling the drape over the monitor. By having a cuff, the user is assured that their hands are not touching something that is non-sterile as they work their way along the monitor. Tear strips 224 are used to control unfolding of the drape during installation. Tear strips 224 hold the drape in its folded position (as shown for example in FIG. 9C), and as the user installs the drape, tear strips 224 are broken as the drape is pulled back over the monitor.

Figure 10A:
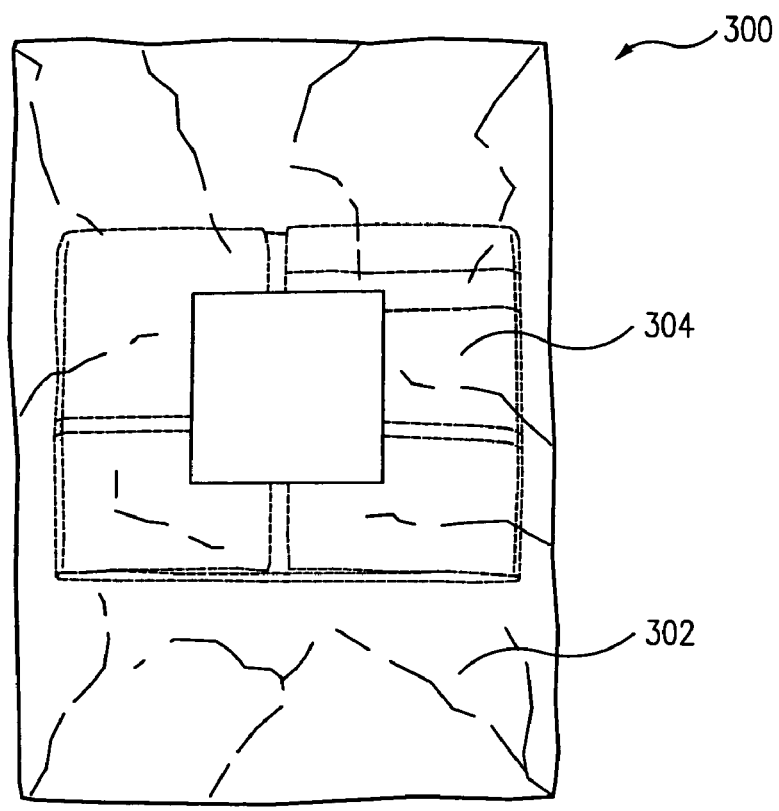
FIGS. 10A-10J are views of an ECM (camera arm) drape in accordance with an embodiment of the present invention.

Referring now to FIGS. 10A-10J, an endoscope camera manipulator (ECM) (camera arm) drape package 300 including an ECM drape 304 that is part of sterile drape 70 (described above with reference to FIG. 3A) is shown. ECM drape 304 may be a connected or disconnected section of sterile drape 70. FIG. 10A shows ECM drape package 300 including an ECM drape pouch 302 with ECM drape 304 folded inside. The ECM drape is a disposable sterile drape assembly designed to establish a sterile barrier between the non-sterile ECM camera arm and the sterile field of the surgical procedure. Advantageously, various features of ECM drape 304 aid the draping and installation process.

Figure 10B:
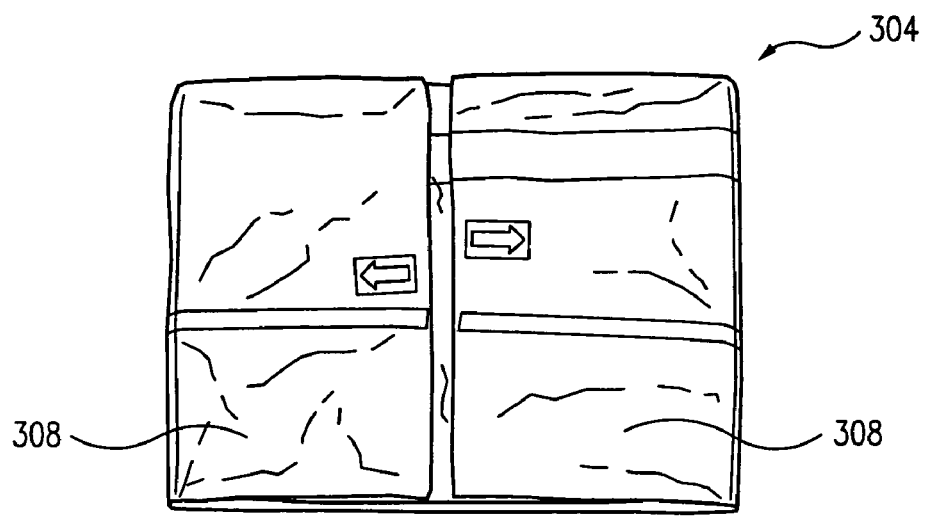
Figure 10C:
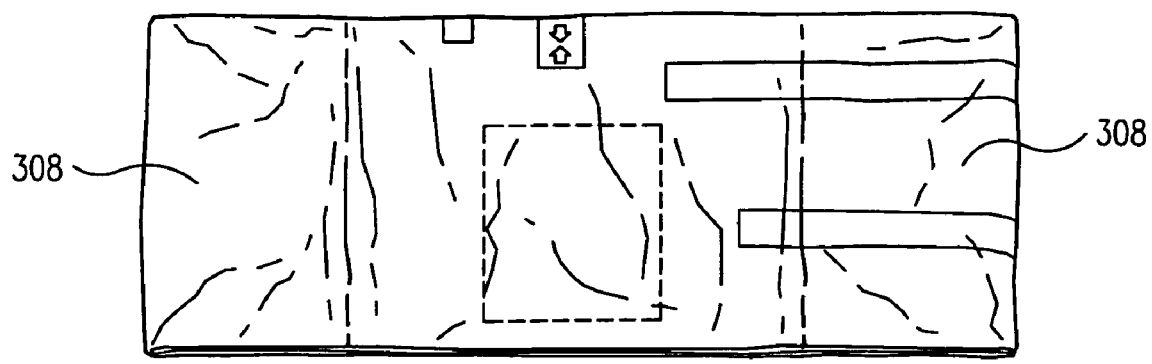
Figure 10D:
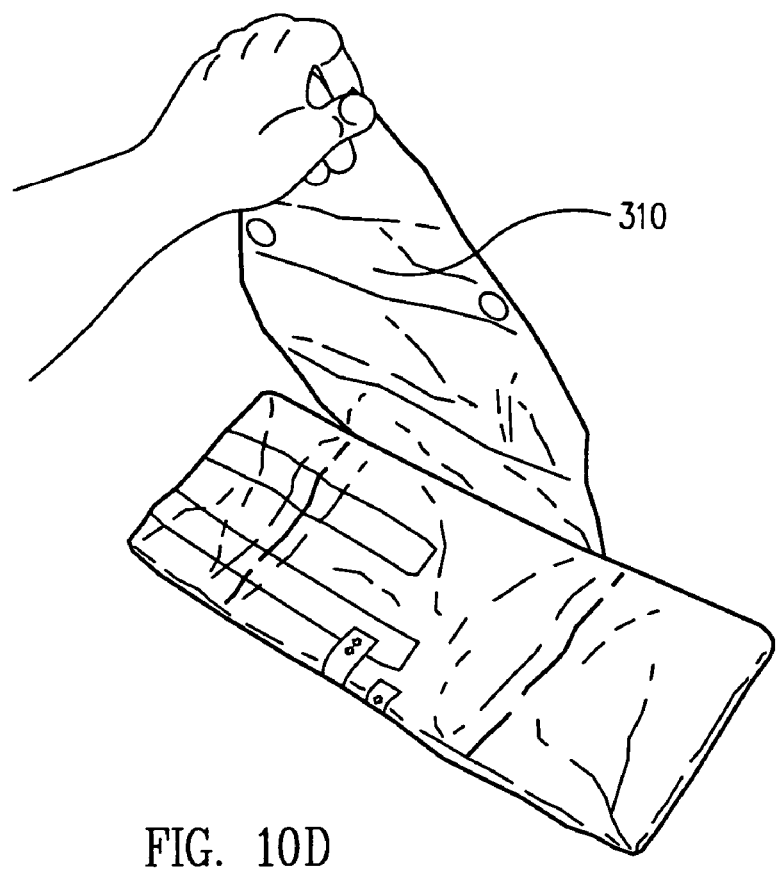
Figure 10E:
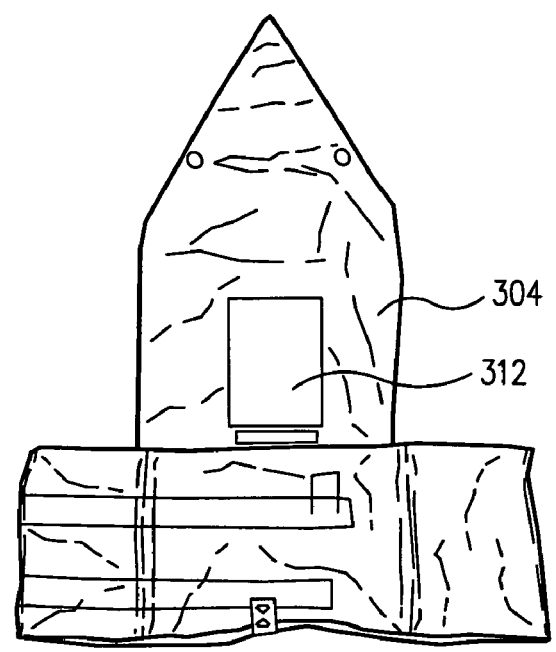
Figure 10F:
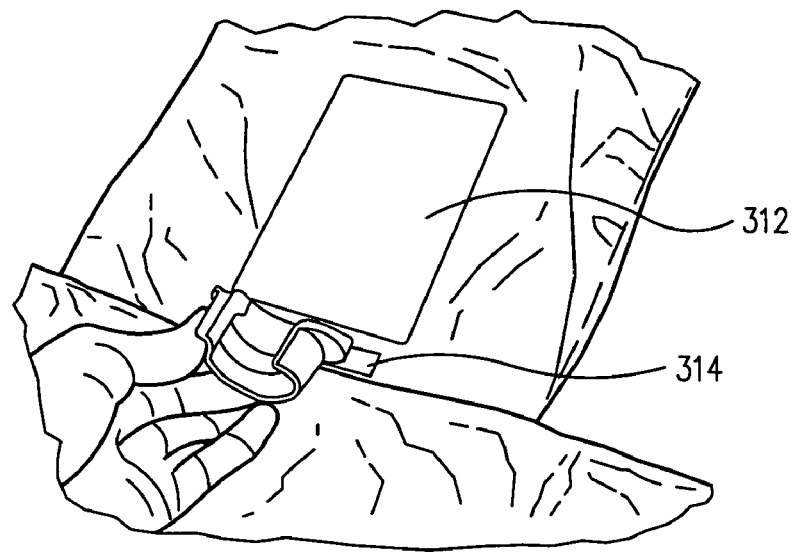

FIG. 10B shows ECM drape 304 removed from pouch 302. ECM drape 304 is folded with two flaps 308 and arrow labels show the direction for unfolding of flaps 308. FIG. 10C shows ECM drape 304 with flaps 308 unfolded. FIG. 10D shows visual indicators 310 for positioning or locating ECM drape 304 on the ECM arm. Visual indicators 310 include a patch 312 and a patch 314 as described in more detail below with respect to FIG. 10F. FIG. 10E shows a closed end of ECM drape 304 partially unfolded. FIG. 10F shows a reinforcement patch 312 used to keep ECM drape 304 from interfering when installing a camera on the ECM arm. Also shown is a peel-and-stick patch 314 for attaching a camera sterile adaptor.

Figure 10G:
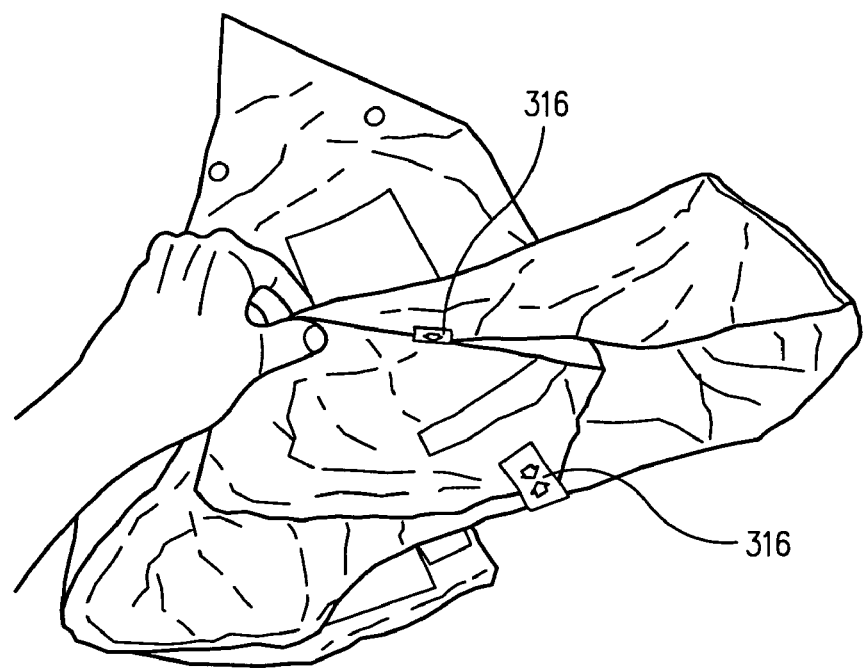
Figure 10H:
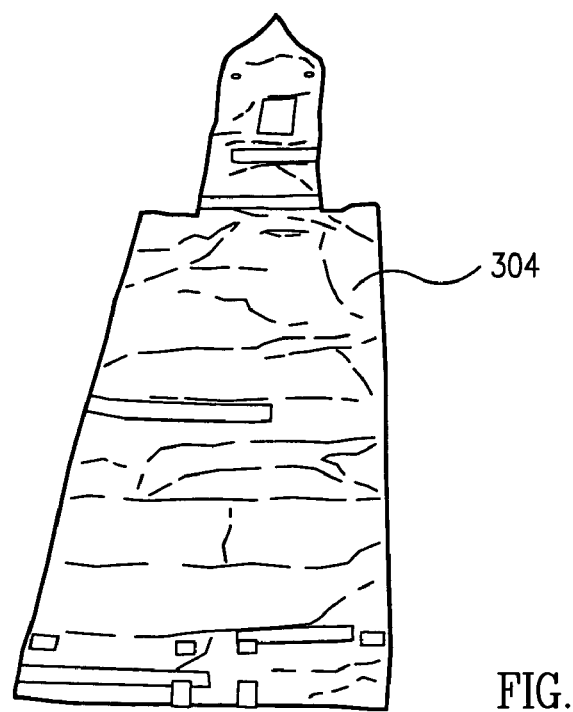

FIG. 10G shows tear strips 316 that define the main entrance/exit of the drape through which the ECM arm enters or exits ECM drape 304. ECM drape 304 is packaged such that the folded drape can be first placed over the ECM arm. The drape is set in this initial position by using tear strips 316 which allow for the controlled unfolding of the drape by tearing when pulled on with the necessary force. The user pulls ECM drape 304 along the length of the ECM arm by placing their hands in cuffs 323 (FIG. 10I) and pulling the drape along the ECM arm. FIG. 10H shows ECM drape 304 fully unfolded.

Figure 10I:
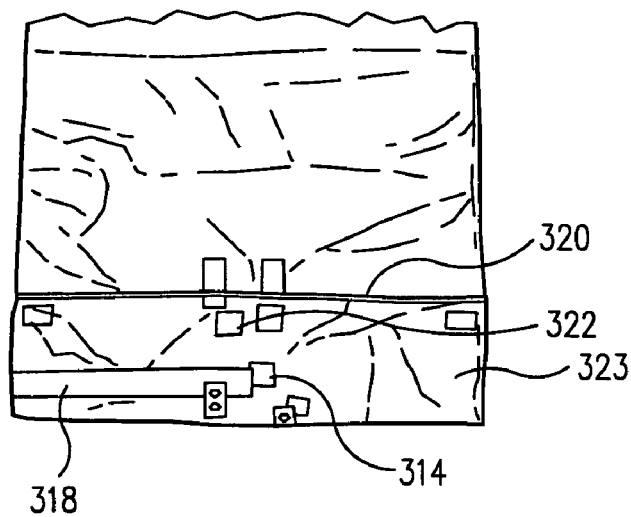

FIG. 10I shows a strap 318 at the end of ECM drape 304, a blue tape 320 at the edge of a cuff 323, a slit 322 in cuff 323 for wrapping the ECM drape around the monitor mount, and peel-and-stick patches 314. ECM drape 304 includes an integral cuff 323 at the end of the drape. The sterile scrub nurse may place his or her hands into these cuffs when pulling the drape along the ECM arm, thereby assuring the user that their hands are not touching something that is non-sterile as they work their way along the ECM arm. Blue tape 320 acts as a physical marker on the drape to designate the sterile and non-sterile ends. By having blue tape 320 act as a marker, a non-sterile person can know to pull on the non-sterile side if assisting the sterile scrub nurse.

Figure 10J:
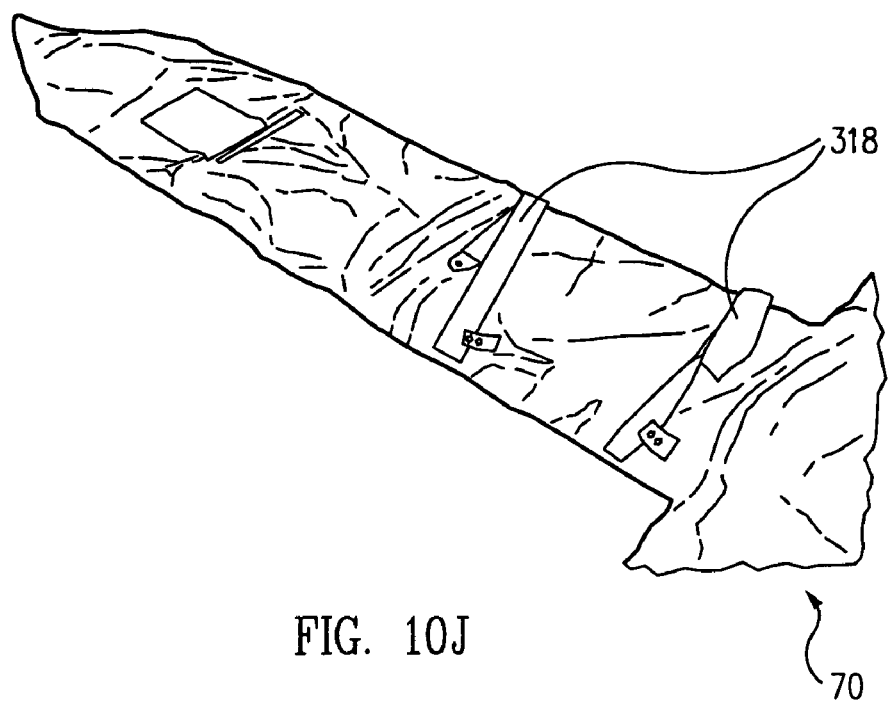

FIG. 10J shows straps 318 which help to control the ECM drape and reduce the visual size of the drape (i.e., reduce the volume of or space taken up by the unfolded drape). There is one strap proximate the cannula mount area, another strap proximate a "link 3" of the ECM arm, and another strap proximate the "setup arm" (e.g., arm 42 of FIGS. 4 and 5) onto which the ECM arm is mounted.

Figure 11A:
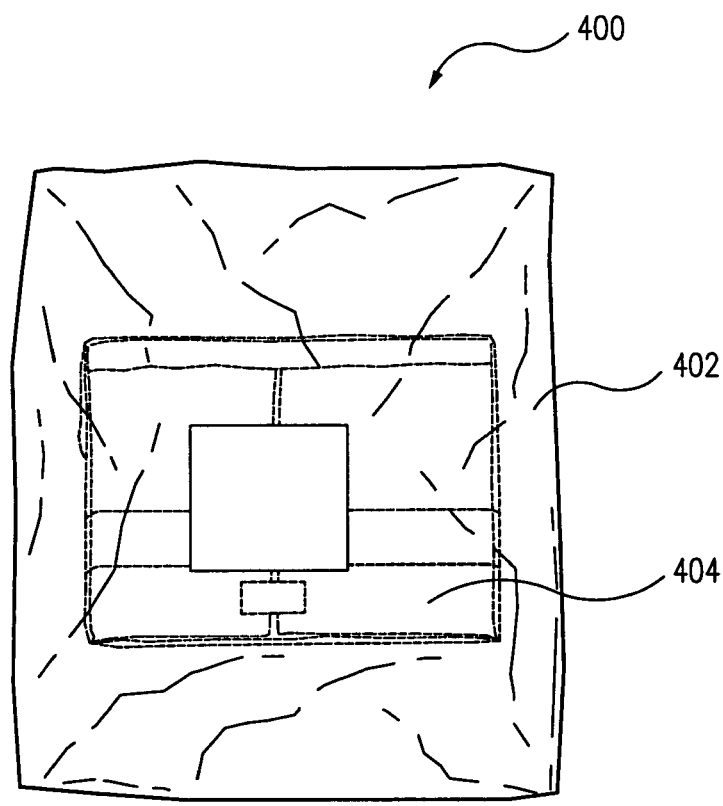

Referring now to FIGS. 11A-11M, a patient side manipulator (PSM) drape package 400 including a PSM drape 404 that is part of sterile drape 70 (described above with reference to FIG. 3A) is shown. PSM drape 404 may be a connected or disconnected section of sterile drape 70. FIG. 11A shows PSM drape package 400 including a PSM drape pouch 402 with PSM drape 404 folded inside. The PSM drape is designed to establish a sterile barrier between the non-sterile PSM arms and the sterile field of the surgical procedure. PSM drape 404 includes an integral instrument sterile adaptor (ISA) permanently mounted on the drape, with the complete assembly including the ISA, which is used to engage a surgical tool. Embodiments of applicable adaptors, tools, or accessories are described for example in U.S. Pat. Nos. 6,331,181, 6,491,701, and 6,770,081, the full disclosures of which (including disclosures incorporated by reference therein) are incorporated by reference herein for all purposes. Thus, the drape is completely disposable in one embodiment. Advantageously, various features of the PSM drape aid the draping and installation process.

Figure 11B:
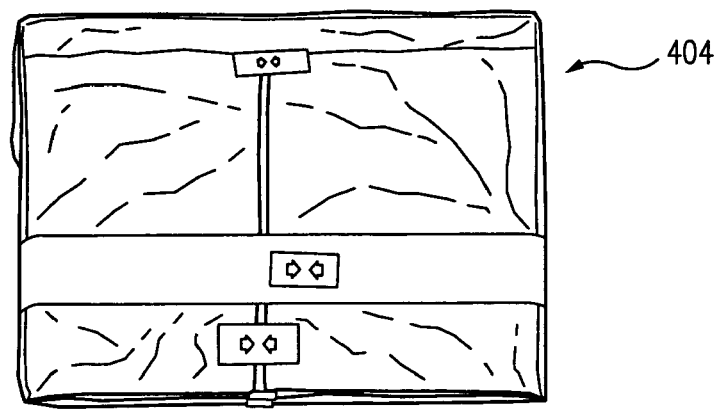
Figure 11C:
Figure 11D:
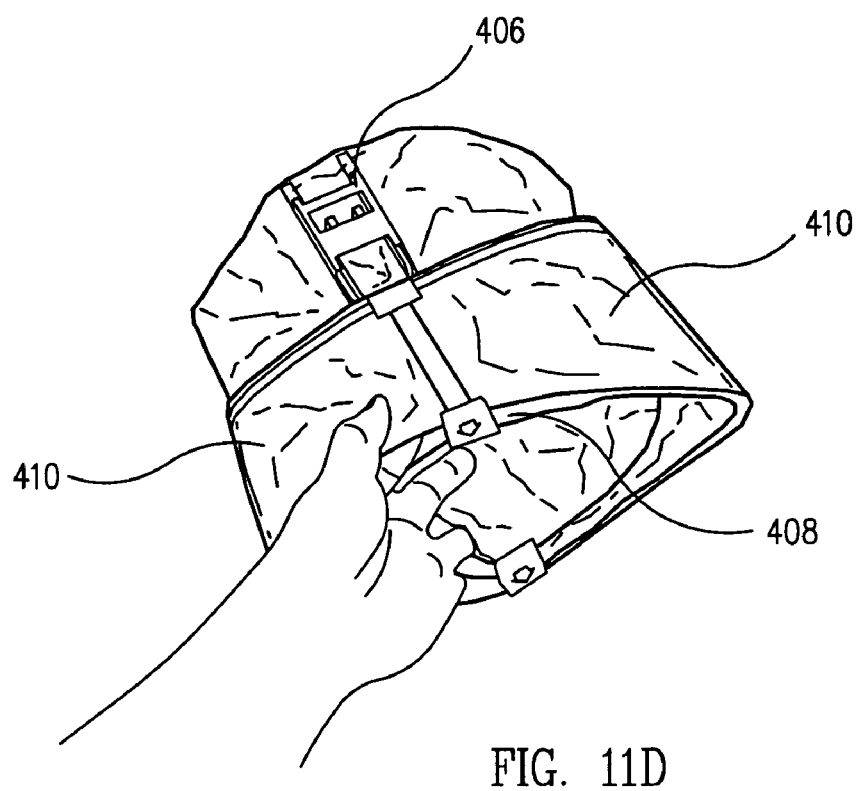
Figure 11E:
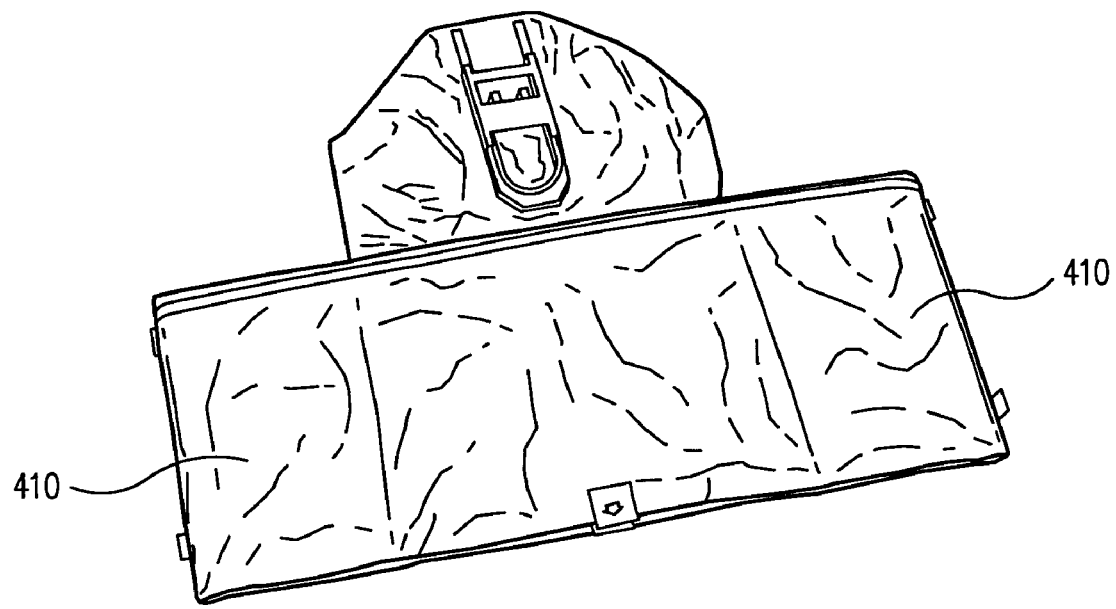
Figure 11F:
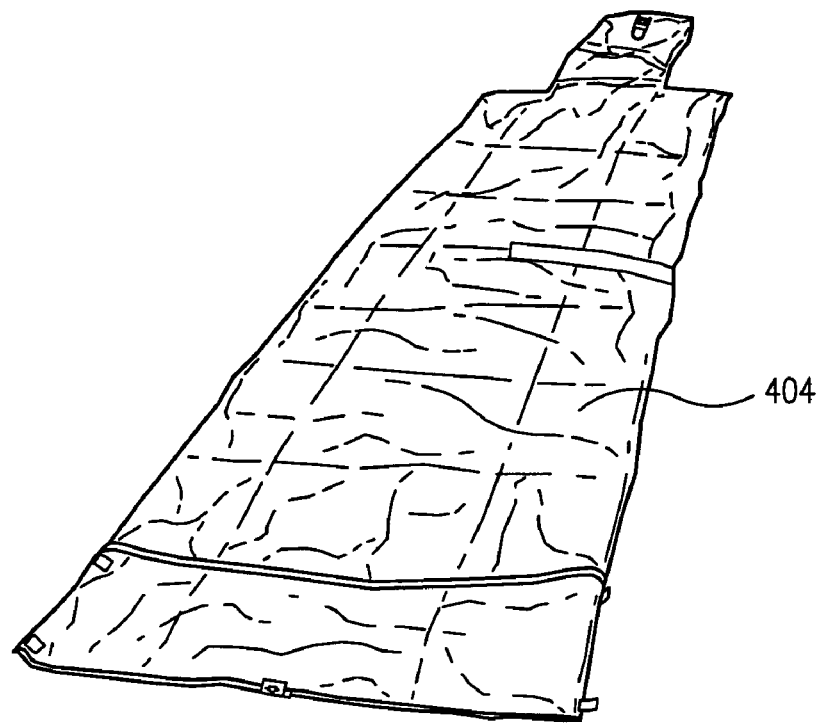

FIG. 11B shows PSM drape 404 removed from pouch 402. FIG. 11C shows an example of a sterile adaptor 406 permanently mounted to PSM drape 404 proximate a closed end of PSM drape 404. FIG. 11D shows tear strips 408 that define the main hole in the folded PSM drape and folded flaps 410. FIG. 11E shows flaps 410 unfolded, and FIG. 11F shows PSM drape 404 completely unfolded. PSM drape 404 is packaged so that the folded drape can be first placed over the PSM arm and then the permanently mounted sterile adaptor 406 is attached to the PSM arm by first locating a front tongue feature into a bracket on the PSM arm followed by swinging the other end of the sterile adaptor until it engages a latch on the PSM arm. PSM drape 404 is maintained in this initial position by using tear strips 408 which allow for the controlled unfolding of the drape by tearing when pulled on with the necessary force. The user pulls the drape along the length of the PSM arm by placing their hands in integral cuffs 412 (FIG. 11G) and pulling the drape along the PSM arm.

FIGS. 11G1 and 11G2 show an integral cuff 412 at the open end of PSM drape 404, the edge of cuff 412 including a blue tape 411. The sterile scrub nurse may place his or her hands into the cuff when pulling the PSM drape along the PSM arm, and by using the cuff, the user is assured that their hands are not touching something that is non-sterile as they work their way along the PSM arm. Blue tape 411 acts as a physical marker on the drape to designate the sterile and non-sterile ends. By having this marker, a non-sterile person can know to pull on the non-sterile side when assisting the sterile scrub nurse.

Figure 11H:
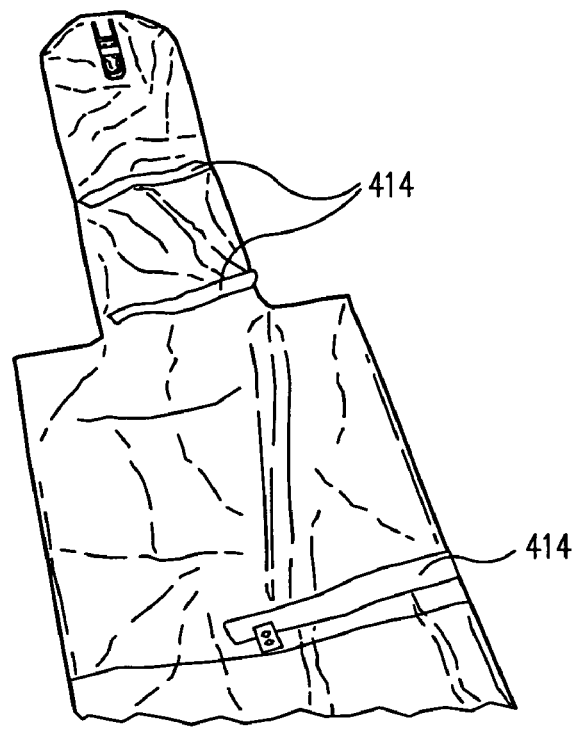

FIG. 11H shows straps 414 on the drape to help control the drape and reduce the visual size of the drape (i.e., reduce the volume of or space taken up by the unfolded drape). One strap is proximate the cannula mount area, another strap is proximate a "link 3" of the PSM arm, and another strap is along a "setup arm" (e.g., arm 42 of FIGS. 4 and 5) onto which the PSM arm is mounted.

Figure 11I:
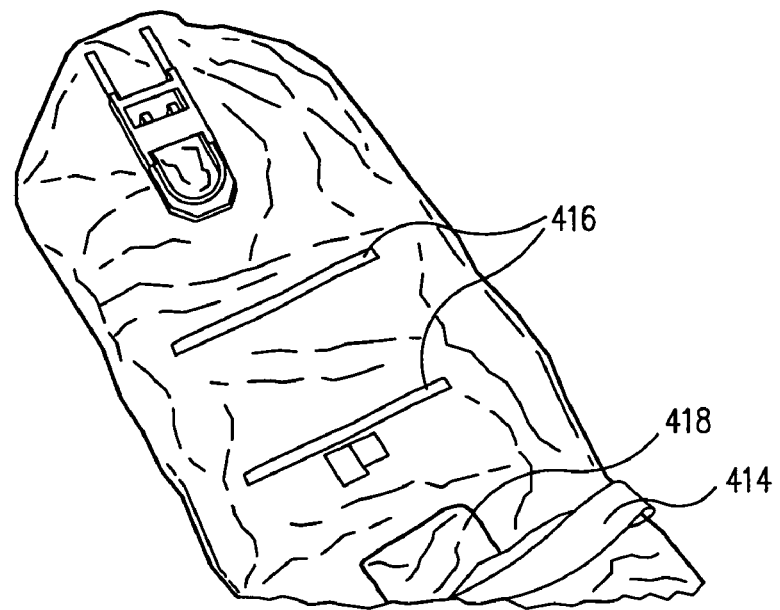

FIG. 11I shows strips 416 along the insertion axis and a cannula mount pouch 418. A cannula mount pouch that may be used is disclosed in co-pending U.S. patent application Ser. No. 11/240,087, filed Sept. 30, 2005, the contents of which is incorporated by reference herein for all purposes. Strips 416 are malleable strips on the drape in an insertion axis area. Strips 416 are attached to the drape between the sterile adaptor and the cannula mount area. Once the drape is installed on the PSM arm, the user can deform the malleable strips 416 to help fold back excess drape material. By being able to fold back and secure excess drape material, the drape can be made to closely fit the shape of the PSM arm. Advantageously, this reduces the visual size of the system and thereby allows more visibility of the patient and their surroundings to the surgeon or other user(s). Strips 416 are also sufficiently malleable to be able to open up to allow the system to achieve maximum range of motion without tearing the drape.

Figure 11J:
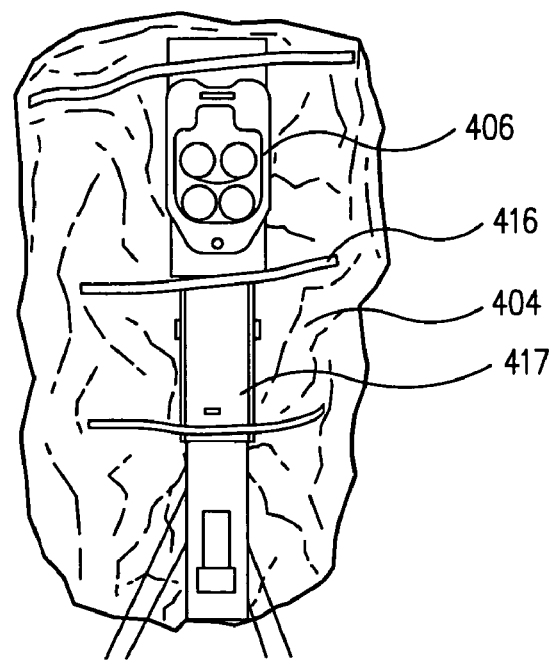
Figure 11K:
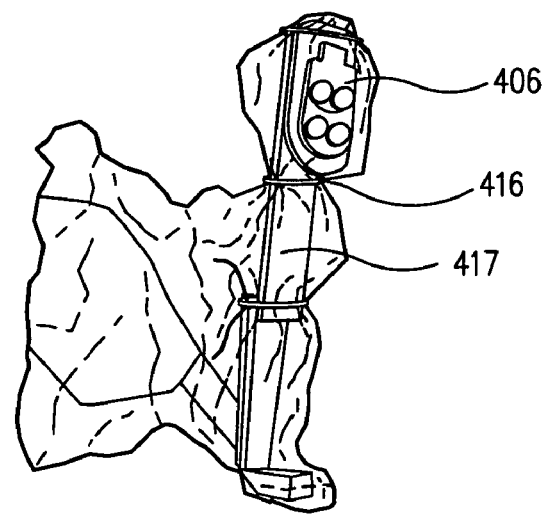
Figure 11L:
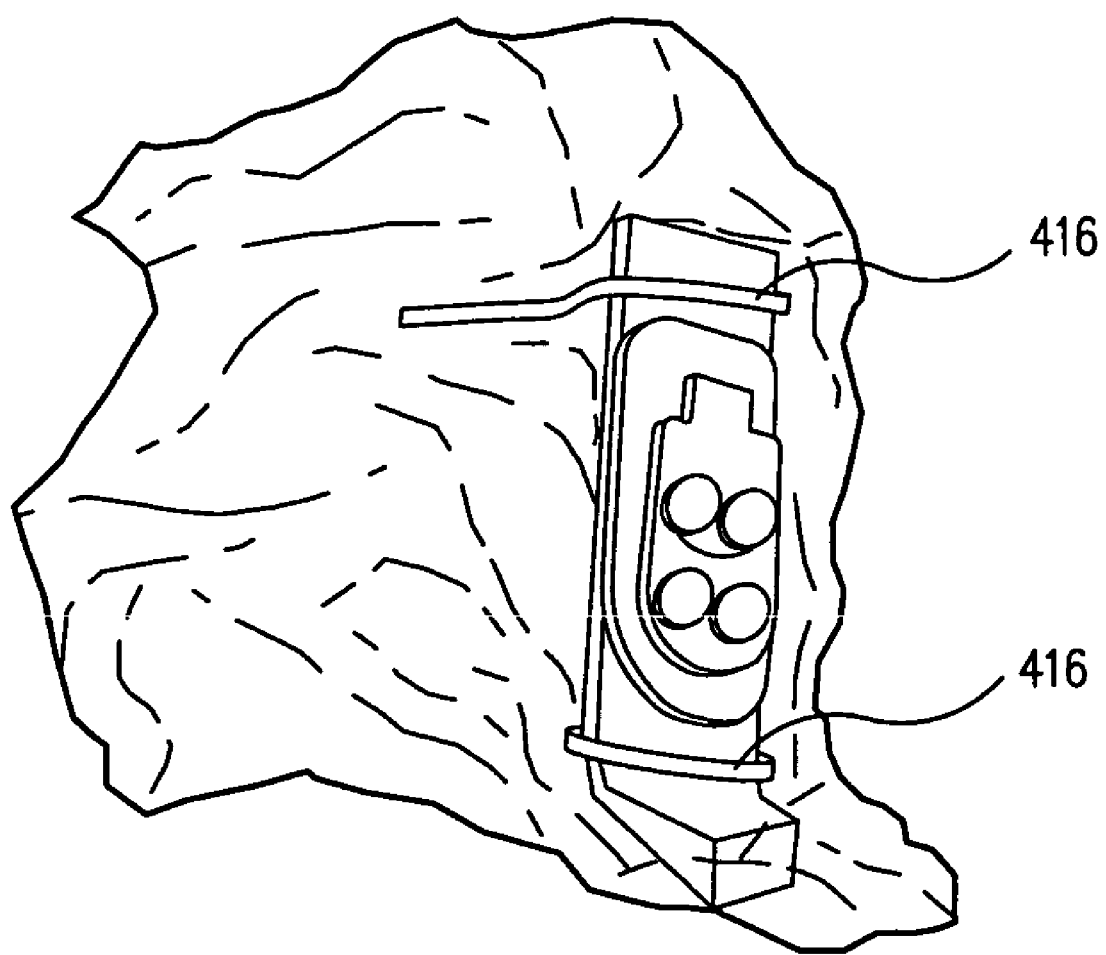

FIG. 11J shows PSM drape 404 over a portion of PSM arm 417 and a sterile adaptor 406 in place prior to strips 416 being bent back by the user. FIG. 11K shows strips 416 after being bent back by the user such that PSM drape 404 more closely fits the shape of the PSM arm, thereby reducing the size of the system. FIG. 11L shows another view of the strips 416 which are pliable enough to be opened for maximum range of motion and which can be reshaped by the user as desired during the procedure.

Drapes 200, 300, and 400 described above are preferably comprised of material of sufficient rigidity and strength to allow proper placement over a monitor and monitor mount, an ECM arm, and a PSM arm, respectively, and to resist tearing even under application of cyclical loads in various directions, but are preferably comprised of material of sufficient flexibility to allow movement with the active sections of the manipulator arms. Drapes 200, 300, and 400 may be comprised of various durable materials, and in one example is comprised of polyethylene, polyurethane, polycarbonate, or mixtures thereof. In one embodiment, drapes 200, 300, and 400 can be vacuum formed as part of a single drape or as separate drapes that can be attached to the main sterile drape 70 via adhesive, heat, RF welding, or other means. In another embodiment, drapes 200, 300, and 400 may be used as disconnected drapes (but possibly adjacent to one another or with overlap) to cover different portions of the surgical robot system.

Advantageously, the drapes of the present invention increase visualization of the patient by reducing the size of the drapes with more form fitting features, allow for quick and simple installation, and improve the instrument sterile adaptor feature. The drapes of the present invention also maintain the sterility of a monitor screen, in particular a touch screen monitor, allow for sound to be transmitted to a microphone on the monitor drape while maintaining sterility, and reduce glare and wrinkles of the drape in front of the monitor screen.

Embodiments described above illustrate but do not limit the invention. It should also be understood that numerous modifications and variations are possible in accordance with the principles of the present invention. For example, although drapes for particular parts of the robotic surgical system are described in the embodiments above, other shapes and cavities for receiving other surgical system parts are within the scope of the present invention. Accordingly, the scope of the invention is defined only by the following claims.

We claim:

1. A sterile drape to cover a non-sterile portion of a robotic surgical system, the sterile drape comprising:
   an exterior surface adjacent to a sterile field for performing a surgical procedure;
   an interior surface forming a cavity for receiving the non-sterile portion of the robotic surgical system;
   an integral cuff including a permanently turned-up fold of the exterior and interior surfaces at an open end of the cavity and a marker on the permanently turned-up fold designating a sterile side and a non-sterile side of the drape; and
   a fastener coupled to the exterior surface for securing the sterile drape to the non-sterile portion of the robotic surgical system for reducing the volume of the cavity formed by the sterile drape.

2. The sterile drape of claim 1, wherein the exterior surface includes a peel-and-stick patch.

3. The sterile drape of claim 1, wherein the drape is comprised of a material selected from the group consisting of polyethylene, polyurethane, and polycarbonate.

4. The sterile drape of claim 1, wherein the cavity receives the non-sterile portion of the robotic surgical system selected from the group consisting of a monitor, a manipulator arm, and an endoscope camera manipulator arm.

5. The sterile drape of claim 1, wherein the exterior surface and the interior surface of the drape is couplable to another drape portion.

6. The sterile drape of claim 1, wherein the fastener includes malleable strips and straps.

7. The sterile drape of claim 1, wherein the exterior and interior surfaces include a window for positioning adjacent to a monitor screen.

8. The sterile drape of claim 7, wherein the window has a static charge.

9. The sterile drape of claim 1, wherein the exterior and interior surfaces include an instrument sterile adaptor for engaging a surgical tool and the non-sterile portion of the robotic surgical system, the sterile adaptor being configured to transfer signals between the surgical tool and the non-sterile portion of the robotic surgical system.

10. The sterile drape of claim 1, wherein the exterior and interior surfaces include a venting portion.

11. The sterile drape of claim 1, wherein the open end further includes a purse string.

12. The sterile drape of claim 1, wherein the open end further includes a tear strip.

13. The sterile drape of claim 1, wherein the integral cuff includes a visual marker.

14. A sterile drape comprising:
   an exterior surface adjacent to a sterile field for performing a surgical procedure;
   an interior surface forming a cavity for receiving a manipulator arm of a robotic surgical system;
   an integral cuff including a permanently turned-up fold of the exterior and interior surfaces at an open end of the cavity and a marker on the permanently turned-up fold designating a sterile side and a non-sterile side of the drape; and
   a plurality of fasteners on the exterior surface for securing the sterile drape to the manipulator arm.

15. The drape of claim 14, wherein the exterior surface includes a peel-and-stick patch.

16. The drape of claim 14, wherein the exterior and interior surfaces are comprised of a material selected from the group consisting of polyethylene, polyurethane, and polycarbonate.

17. The drape of claim 14, wherein the plurality of fasteners include malleable strips and straps.

18. The drape of claim 14, wherein the exterior and interior surfaces include a window for positioning adjacent to a monitor screen.

19. The drape of claim 18, wherein the window has a static charge.

20. The drape of claim 14, wherein the exterior and interior surfaces include an instrument sterile adaptor, the sterile adaptor being configured to transfer signals between a surgical tool and the manipulator arm of the robotic surgical system.

21. The drape of claim 14, wherein the exterior and interior surfaces include a venting portion.

22. A method of draping a robotic surgical system, the method comprising:
   providing a sterile drape including:
      an exterior surface adjacent to a sterile field for performing a surgical procedure;
      an interior surface forming a cavity for receiving a non-sterile portion of the robotic surgical system;
      an integral cuff including a permanently turned-up fold of the exterior and interior surfaces at an open end of the cavity and a marker on the permanently turned-up fold designating a sterile side and a non-sterile side of the drape; and
      a fastener for securing the sterile drape to the non-sterile portion of the robotic surgical system;
   positioning the open end at a portion of the robotic surgical system;
   holding the integral cuff to unfold the sterile drape over the portion of the robotic surgical system; and
   securing the sterile drape to the portion of the robotic surgical system using the fastener.

23. The method of claim 22, further comprising coupling an instrument sterile adaptor integrated with the sterile drape to a manipulator arm of the robotic surgical system.

24. The method of claim 22, further comprising positioning a window and a venting portion of the sterile drape proximate a monitor of the robotic surgical system.

25. The method of claim 24, further comprising unfolding the sterile drape such that the window is not creased or folded.

26. The method of claim 24, wherein the window is positioned adjacent to a monitor screen via static charge.

* * * * *